(12) United States Patent
Campbell et al.

(10) Patent No.: US 9,507,004 B2
(45) Date of Patent: Nov. 29, 2016

(54) ELECTRON SPIN RESONANCE SPECTROMETER AND METHOD FOR USING SAME

(71) Applicants: NATIONAL INSTITUTE OF STANDARDS AND TECHNOLOGY, Gaithersburg, MD (US); The Penn State Research Foundation, University Park, PA (US)

(72) Inventors: Jason P. Campbell, Frederick, MD (US); Kin P. Cheung, Rockville, MD (US); Jason T Ryan, Frederick, MD (US); Patrick M. Lenahan, Boalsburg, PA (US)

(73) Assignees: THE GOVERNMENT OF THE UNITED STATES OF AMERICA, AS REPRESENTED BY THE SECRETARY OF COMMERCE, Washington, DC (US); THE PENN STATE RESEARCH FOUNDATION, University Park, PA (US)

( * ) Notice: Subject to any disclaimer, the term of this patent is extended or adjusted under 35 U.S.C. 154(b) by 478 days.

(21) Appl. No.: 14/244,494

(22) Filed: Apr. 3, 2014

(65) Prior Publication Data

US 2014/0210473 A1    Jul. 31, 2014

Related U.S. Application Data

(60) Provisional application No. 61/860,283, filed on Jul. 31, 2013.

(51) Int. Cl.
*G01V 3/00* (2006.01)
*G01R 33/60* (2006.01)
*G01N 24/10* (2006.01)

(52) U.S. Cl.
CPC .............. *G01R 33/60* (2013.01); *G01N 24/10* (2013.01)

(58) Field of Classification Search
USPC ......................................................... 324/316
See application file for complete search history.

(56) References Cited

U.S. PATENT DOCUMENTS

| 4,537,731 | A |   | 8/1985  | Billet    |                       |
|-----------|---|---|---------|-----------|-----------------------|
| 5,233,303 | A | * | 8/1993  | Bales     | G01R 33/60<br>324/316 |
| 5,654,636 | A | * | 8/1997  | Sweedler  | G01R 33/46<br>324/307 |
| 5,828,216 | A | * | 10/1998 | Tschudin  | G01R 33/3621<br>324/300 |
| 5,865,746 | A | * | 2/1999  | Murugesan | G01R 33/60<br>600/410 |

(Continued)

OTHER PUBLICATIONS

Rubinson et al., "Modified, short-circuited coaxial-line resonators for CW-EPR," Journal of Magnetic Resonance a 117, 91 (1995).

(Continued)

*Primary Examiner* — Rodney Fuller
(74) *Attorney, Agent, or Firm* — Toby D. Hain

(57) ABSTRACT

An electron spin resonance spectrometer includes a bridge to transmit an excitation frequency and to receive a signal frequency; a probe electrically connected to the bridge and comprising: a first conductor in electrical communication with the bridge to transmit the signal frequency to the bridge; a shorting member electrically connected to the first conductor to transmit the excitation frequency to a sample, to produce the signal frequency, and to transmit the signal frequency to the first conductor; and a second conductor electrically connected to the shorting member; and a magnet disposed proximate to the probe.

20 Claims, 12 Drawing Sheets

(56) References Cited

U.S. PATENT DOCUMENTS

| | | | |
|---|---|---|---|
| 5,900,618 A | 5/1999 | Anlage | |
| 7,403,008 B2 * | 7/2008 | Blank | G01R 33/60 324/316 |
| 7,809,425 B2 * | 10/2010 | Hashimshony | A61B 5/053 600/411 |
| 8,067,937 B2 | 11/2011 | Blank | |
| 8,721,565 B2 * | 5/2014 | Hashimshony | A61B 5/4381 600/363 |
| 2005/0021019 A1 * | 1/2005 | Hashimshony | A61B 5/053 606/32 |
| 2006/0286492 A1 * | 12/2006 | Morrisroe | F23C 99/001 431/2 |

OTHER PUBLICATIONS

Rubinson et al., "FT-EPR with a Nonresonant Probe," Journal of Magnetic Resonance 132, 255 (1998).

Rubinson et al., "Broadband (up to 10 GHz) Electron Paramagnetic Resonance Spectrometer," Rev. Sci. Instruments 60, 392 (1989).

Altink et al., "Sensitive Electron Paramagnetic Resonance Spectrometer for Studying Defects in Semiconductors," Rev. Sci. Instruments 63, 5742 (1992).

An et al., "Local Excitation of Ferromagnetic Resonance and its Spatially Resolved Detection with an Open-Ended Radio-Frequency Probe," IEEE Mag. Lett. 1, 3500104 (2010).

Anlage et al., "Near-Field Microwave Microscopy of Materials Properties," Microwave Superconductivity, Weinstock and Nisenoff (eds.), 239 (Kluwer, 2001).

Hagen et al., "Broadband Transmission EPR Spectroscopy," PLOS One 8, 1 (2013).

Hahn et al., "EPR Imaging at a Few Megahertz Using Squid Detectors," NASA Tech Briefs, 34 (Jan. 2010).

Jang et al., "Broadband Electron Spin Resonance at Low Frequency Without Resonant Cavity," Review Scientific Instruments 79, 0146101 (2008).

Li et al., "Near-Field Microwave Microscope and Electron-Spin-Resonance Detection," Applied Optics 45, 2191 (2006).

Sakran et al., "Electron Spin Resonance Microscopic Surface Imaging Using a Microwave Scanning Probe," Applied Phyyics Letter 82, 1479 (2003).

Tabib-Azar et al., "Novel Physical Sensors Using Evanescent Microwave Probes,"Review Scientific Instruments 70, 3381 (1999).

* cited by examiner

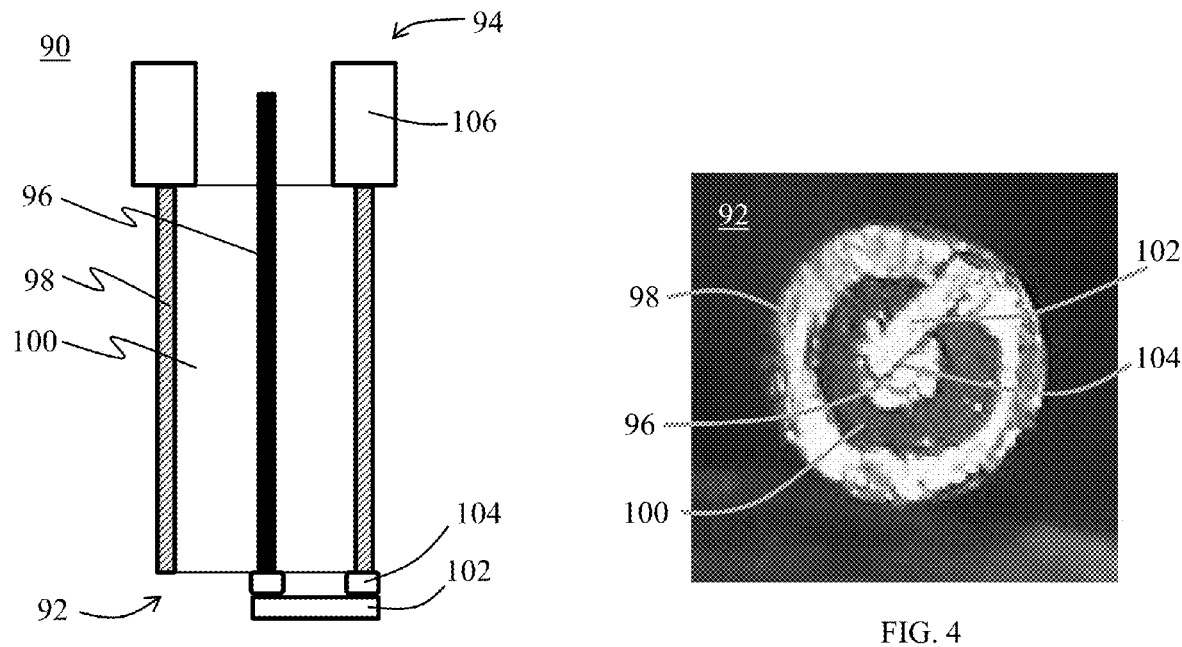
FIG. 3
FIG. 4
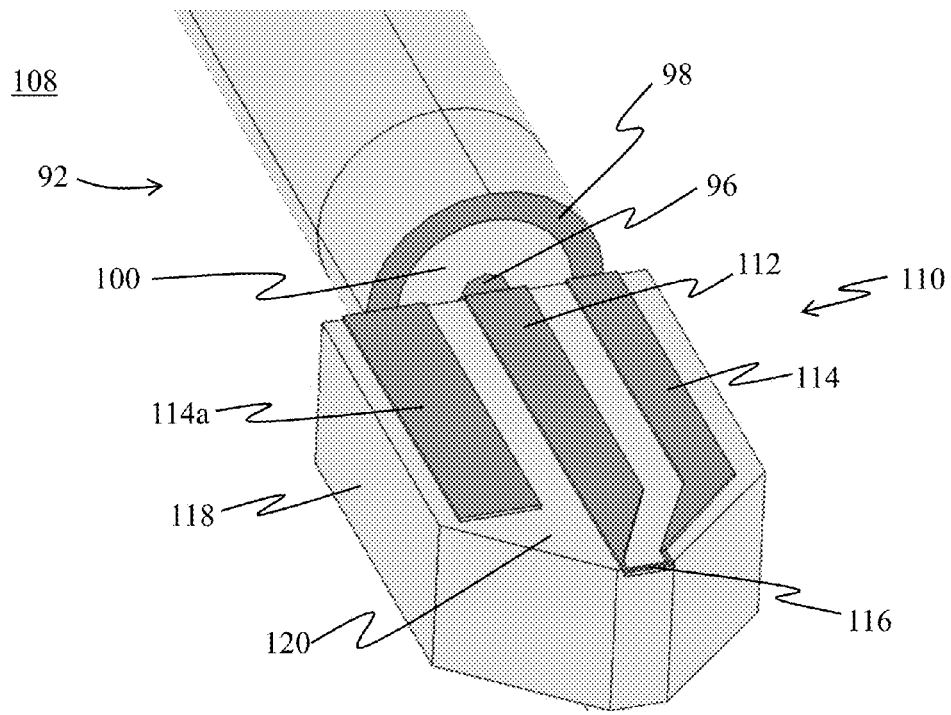
FIG. 5

ELECTRON SPIN RESONANCE SPECTROMETER AND METHOD FOR USING SAME

CROSS REFERENCE TO RELATED APPLICATIONS

This application claims the benefit of U.S. Provisional Patent Application Ser. No. 61/860,283 filed Jul. 31, 2013, the disclosure of which is incorporated herein by reference in its entirety.

STATEMENT REGARDING FEDERALLY SPONSORED RESEARCH

This invention was made with United States government support from the National Institute of Standards and Technology. The government has certain rights in the invention.

BACKGROUND

Over the last several decades, the microelectronics industry grew immensely and had a global impact on advancing commercial industries. Sales of semiconductor components recently made up a substantial fraction of the gross domestic product for many developed countries, which was an outcome of a continual decrease in the size of metal-oxide-silicon field effect transistors (MOSFETs). The miniaturization of MOSFETs resulted in an exponential increase in integrated circuit (IC) performance and a corresponding decrease in the cost of microelectronics as predicted by Moore's Law. MOSFET scaling leveraged performance increases due to reduction of the physical dimensions of the MOSFET device. For example, transistors were produced with a minimum channel dimension of 30 nm. At this size, atomic-scale defects determined the performance and reliability of the transistors, and conventional characterization methods previously used to obtain operating performance of larger transistors were inadequate.

Until a few years ago, continued scaling of microelectronic devices implicated only a crude understanding of atomic-scale defects, which is no longer the case. In current nano-scale device structures, understanding the relationship between atomic-scale defects and electronic transport is aided by intimate knowledge of the chemical, physical, and electronic structure of the device. As an example of the need for understanding devices on the atomic-scale, it has been widely reported that room temperature MOSFETs can exhibit drive current fluctuations that are as large as 75% of an amplitude of the drive current. These fluctuations, which are referred to as random telegraph noise, limit further MOSFET scaling. However, the origin of the fluctuations is not understood. To advance development of microelectronics, overcoming the detrimental effects of atomic-scale defects will occur by understanding such defects, and amelioration of these defects involves detailed spectroscopic knowledge of their creation kinetics. Current technologies largely are inadequate at this level of detail.

Accordingly, methods and equipment for characterization of atomic-scale defects would be advantageous and would be favorably received in the art.

BRIEF DESCRIPTION

The above and other deficiencies are overcome by, in an embodiment, an electron spin resonance spectrometer comprising: a bridge to transmit an excitation frequency and to receive a signal frequency; a probe electrically connected to the bridge and comprising: a first conductor in electrical communication with the bridge to transmit the signal frequency to the bridge; a shorting member electrically connected to the first conductor to transmit the excitation frequency to a sample, to produce the signal frequency, and to transmit the signal frequency to the first conductor; and a second conductor electrically connected to the shorting member; and a magnet disposed proximate to the probe.

Further disclosed is a method for acquiring an electron spin resonance spectrum, the method comprising: disposing a sample in an electron spin resonance spectrometer comprising: a bridge comprising a sample arm and a reference arm; a probe electrically connected to the bridge and comprising: a first conductor electrically connected to the bridge; a shorting member electrically connected to the first conductor; and a second conductor electrically connected to the shorting member; a detector electrically connected to the bridge; a magnet disposed proximate to the probe and the sample; and a modulation coil interposed between the magnet and the sample; transmitting an excitation frequency from an excitation source to the sample through the sample arm and the shorting member; modulating a magnetic field present at the sample from the magnet at a reference frequency applied to the modulation coil; absorbing, by the sample, the excitation frequency; producing a signal frequency at the shorting member; transmitting the signal frequency from the shorting member toward the detector; combining the signal frequency from the sample arm and the excitation frequency from the reference arm to produce a detection frequency; and detecting, by the detector, the detection frequency as a function of changing the excitation frequency or a magnetic field strength present at the sample to acquire the electron spin resonance spectrum, wherein the sample is disposed external to the probe, the magnet, and the modulation coil.

BRIEF DESCRIPTION OF THE DRAWINGS

The following descriptions should not be considered limiting in any way. With reference to the accompanying drawings, like elements are numbered alike:

FIG. 3 shows a longitudinal cross-section of a probe;

FIG. 4 shows an end view of a probe;

FIG. 5 shows a perspective view of a probe that includes a lumped circuit shorting member;

DETAILED DESCRIPTION

A detailed description of one or more embodiments is presented herein by way of exemplification and not limitation.

It has been found that an electron spin resonance spectrometer herein disclosed is highly sensitive and produces information on, e.g., atomic scale defects. Moreover, the electron spin resonance spectrometer includes a probe that is operable as a surface scanning probe or as a probe for bulk materials that provides spectroscopic characterization of, e.g., single defect centers with nano-scale spatial resolution. Advantageously, the probe can be a near-field probe. In addition to detecting single defect centers, the electron spin resonance spectrometer provides comprehensive spectroscopic information necessary to understand their physical and chemical nature. Moreover, the electron spin resonance spectrometer is arranged so that electron spin resonance spectra are acquired without a cavity of a resonator. Consequently, sample sizes are not limited to, e.g., a cavity size as in a conventional electron spin resonance spectrometer. Furthermore, the electron spin resonance spectrometer herein operates in a continuous wave mode or a pulsed mode, and a detection scheme applicable to the electron spin resonance spectrometer includes homodyne detection or superheterodyne detection.

Figure 1:
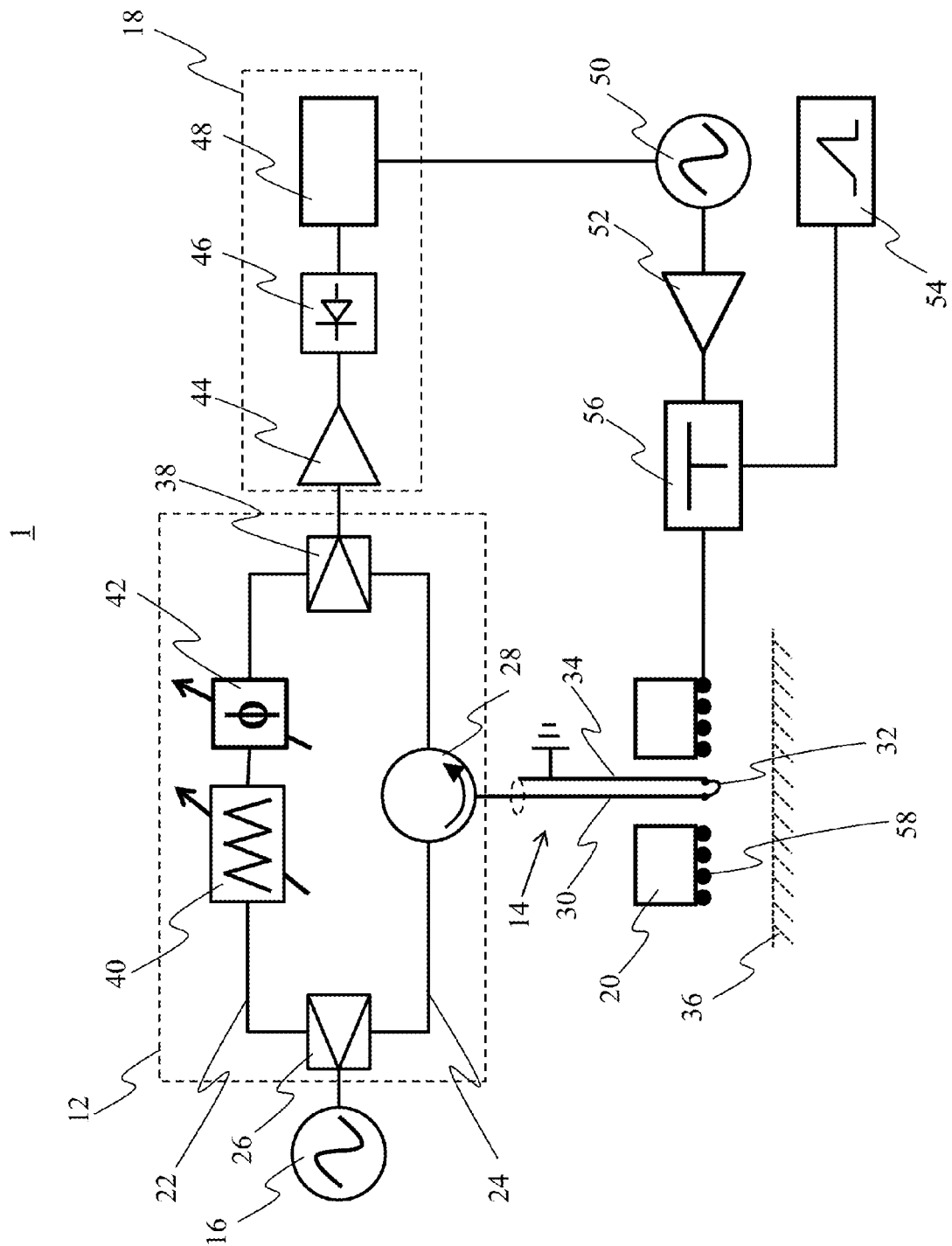
FIG. 1 shows a diagram of an embodiment of an electron spin resonance spectrometer.

According to an embodiment as shown in FIG. 1, electron spin resonance spectrometer 1 includes bridge 12 interposedly connected between excitation source 16, probe 14, and detector 18. Excitation source 16 is configured to produce an excitation frequency that is transmitted to bridge 12. Bridge 12 includes reference arm 22 and sample arm 24 arranged such that each arm 22, 24 receives a portion of the excitation frequency via splitter 26. Circulator 28 delivers the excitation frequency to probe 14. At probe 14, first conductor 30 transmits the excitation frequency to shorting member 32. Shorting member 32 subsequently transmits the excitation frequency to second conductor 34. First conductor 32 and second conductor 34 form a conductive pair, which are electrically shorted to one another by shorting member 32.

The excitation frequency is reflected back to circulator 28 from second conductor 34 through shorting member 32 and first conductor 30. Circulator 28 blocks the excitation frequency from being transmitted back in sample arm 24 to splitter 26, excitation source 16, or reference arm 22. Instead, at circulator 28, the excitation frequency reflected from probe 14 is transmitted through sample arm 24 to combiner 38. Concurrently, reference arm 22 communicates the excitation frequency from excitation source 16 through attenuator 40 and phase shifter 42 so that the excitation frequency from sample arm 24 and reference arm 22 are coincident at combiner 38 and can destructively combine. Due to destructive combination of the excitation frequency combined at combiner 38 from reference arm 22 and sample arm 24, bridge 12 is said to be balanced. Phase shifter 42 along reference arm 22 adjusts a phase of the excitation frequency in reference arm 22 to match a phase of the excitation frequency from sample arm 24 at combiner 38. A phase shift of the excitation frequency transmitted to combiner 38 arises from a difference in path lengths along reference arm 22 and sample arm 24. At combiner 38, frequencies input into combiner 38 from reference arm 22 (the excitation frequency) and sample arm 24 (the excitation frequency reflected from shorting member 32 in the absence of absorption by a sample) are either in phase and constructively combine or are out of phase and destructively combine. The resulting superposition of the combination of the excitation frequencies from reference arm 22 and sample arm 24 can be made to have zero amplitude (or approximately zero amplitude) by adjusting phase shifter 42 so that bridge 12 is balanced and produces the combined frequency having zero amplitude or a very low amplitude. However, the presence of the signal frequency at combiner 38 causes bridge 12 to become unbalanced because the signal frequency also includes modulation at the reference frequency (e.g., the reference frequency is a carrier wave for the reflected excitation frequency), which is not present in the excitation frequency transmitted by reference arm 22. For the signal frequency input into combiner 38, the output of combiner 38 is the combined frequency that has a non-zero amplitude due to the unbalanced condition of combiner 38.

In an embodiment, the electron spin resonance spectrometer has a bridge that includes the reference arm to transmit the excitation frequency to the combiner, the sample arm that includes the circulator and is configured to transmit the signal frequency and the excitation frequency reflected by the shorting member to the combiner, and the combiner to balance the bridge and to transmit the combined frequency towards the detector. Here, the bridge is configured to be balanced in the absence of the signal frequency at the combiner, and the bridge is configured to be unbalanced in the presence of the signal frequency at the combiner.

Magnet 20 is disposed proximate to probe 14 of electron spin resonance spectrometer 1, and modulation coil 58 is disposed on a surface of magnet 20. Electron spin resonance spectrometer 1 is configured to receive sample 36 proximate to and externally disposed to shorting member 32 of probe 14, modulation coil 58, and magnet 20. Magnet 20 applies a magnetic field to sample 36, and modulation coil 58 modifies the strength of the magnetic field applied to sample 36. When sample 36 includes an unpaired electron, the applied magnetic field from magnet 20 or modulation coil 58 perturbs the energy levels associated with the magnetic spin quantum number according to the Zeeman effect. Additionally, the unpaired electron may interact with certain nuclear spins of sample 36 via the applied magnetic field, which results in a hyperfine effect among electronic and nuclear angular momenta. As a result, the energy levels associated with the unpaired electron, are split as a function of the magnetic field strength, and a transition between spin states ($m_s=\pm\frac{1}{2}$) of the electron occurs when the excitation frequency is resonant with the energy difference between two magnetic spin states of the unpaired electron. Here, a single unpaired electron is discussed, but sample 36 may contain a plurality of unpaired electrons that potentially are perturbed by the magnetic field. Thus, an electron spin resonance transition (i.e., a transition between electron magnetic spin states given by the magnetic quantum number $m_s$) occurs for sample 36 present in the applied magnetic field from magnet 20 (or as modified by modulation coil 58) when the excitation frequency subjected to sample 36 from shorting member 32 matches the frequency separation between the magnetic sublevels of the unpaired electron. In this manner, sample 36 absorbs some power from the excitation frequency from probe 14 at shorting member 32. As a result, the amount of power of the excitation frequency that is reflected by probe 14 to circulator 28 is less than the reflected power of the excitation frequency in the absence of sample 36 undergoing an electron spin resonance transition. As discussed below, when an electron spin resonance transition occurs, the reflected excitation frequency is referred to as a signal frequency because it includes information about the reference frequency applied to sample 36 from modulation coil 58. Moreover, when sample 36 is absent or sample 36 does not absorb power from the excitation frequency (because the excitation frequency is not resonant with the Zeeman splitting of the energy levels of the unpaired electron), the excitation frequency is reflected from probe 14 to combiner 38 so that bridge 12 remains balanced.

When sample 36 absorbs power from the excitation frequency, the signal frequency is transmitted from shorting member 32 to circulator 28 and combiner 38. However, bridge 12 was balanced with respect to the excitation frequency reflected by probe 14 and not the signal frequency generated at shorting member 32. In the presence of the signal frequency at combiner 38, bridge 12 is unbalanced such that a combined frequency output from combiner 38 has an amplitude that is proportional to the signal frequency (i.e., an amount of power of the excitation frequency that is absorbed by sample 36).

Combiner 38 transmits the combined frequency to detector 18. At detector 18, amplifier 44 amplifies the combined frequency, the amplified combined frequency being detected by detector 46 (e.g., a diode) to produce a detection frequency that is transmitted to and received by phase sensitive detector 48. Besides the detection frequency, phase sensitive detector 48 receives and is referenced (at a frequency and a phase) to the reference frequency from reference oscillator 50.

Reference oscillator 50 produces and transmits the reference frequency to phase sensitive detector 48 as well as modulation coil 58 interposed between magnet 20 and sample 36. Bias tee 56 receives the reference frequency from amplifier 52 and a bias voltage from power source 54 (e.g., a sweep generator) and transmits (as an output to modulation coil 58) the reference frequency biased at the level of the bias voltage. Hence, modulation coil 58 receives the reference frequency biased at a level of the bias voltage so that modulation coil 58 modulates the magnetic field strength from magnet 20 that is applied to sample 36. It is contemplated that modulation coil 58 is configured to receive the bias voltage, the reference frequency, or a combination thereof. In this manner, the signal frequency produced at shorting member 32 is modulated at the reference frequency of reference oscillator 50 corresponding to modulated absorption of sample 36 in the applied magnetic field. In this arrangement, phase sensitive detector 48 is part of a homodyne detection system wherein an absorption of the excitation frequency by sample 36 is modulated at the frequency of the reference frequency, and the amplitude of the absorption is proportional to the number of unpaired electrons (or a defect density) in sample 36 that are within an excitation volume of shorting member 32. Furthermore, absorption by sample 36 occurs at the frequency of the excitation frequency that is resonant with the separation of the electron magnetic spin states due to the strength of the magnetic field from a combination of magnet 20 and modulation coil 58.

According to an embodiment, an electron spin resonance spectrometer includes a bridge to transmit an excitation frequency and to receive a signal frequency and a probe electrically connected to the bridge. The probe includes the first conductor in electrical communication with the bridge to transmit the signal frequency to the bridge; the shorting member electrically connected to the first conductor to transmit the excitation frequency to a sample, to receive the signal frequency from the sample, and to transmit the signal frequency to the first conductor; and the second conductor electrically connected to the shorting member. The electron spin resonance spectrometer further includes the magnet disposed proximate to the probe.

Figure 2:
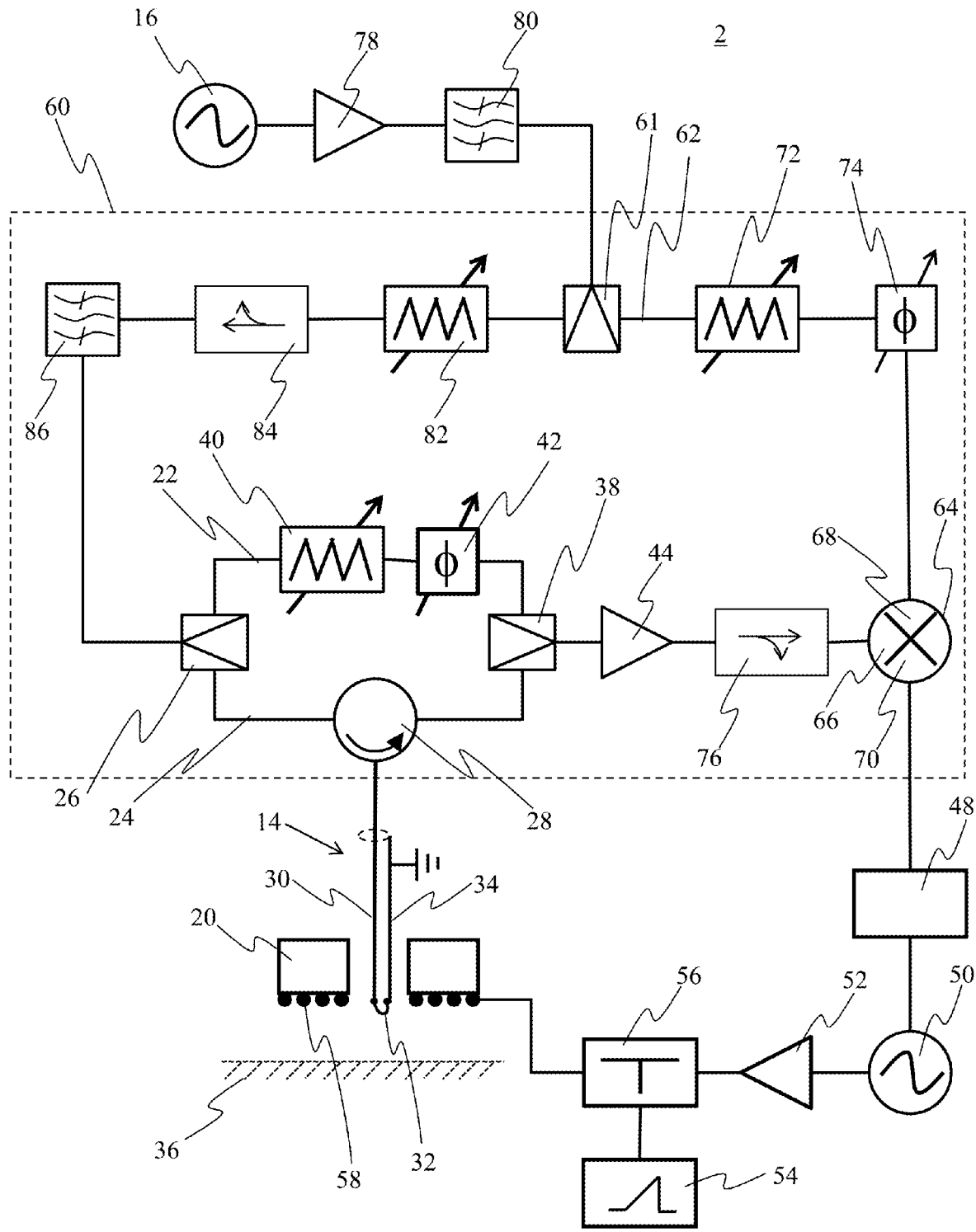
FIG. 2 shows a diagram of an embodiment of an electron spin resonance spectrometer.

In some embodiments, as shown in FIG. 2, electron spin resonance spectrometer 2 includes a heterodyne detection system. Here, an excitation frequency issues from excitation source 16. Amplifier 78 and band pass filter 80 respectively amplify and filter the excitation frequency before it is transmitted to bridge 60 where the excitation frequency is split by splitter 61 and transmitted to local oscillator arm 62. Along local oscillator arm 62, the excitation frequency is subjected to attenuation by attenuator 72 and a phase shift by phase shifter 74 before being received by local oscillator input 68 of mixer 64. Mixer 64 also receives a combined frequency output from combiner 38, which is amplified by amplifier 44.

Besides being transmitted to local oscillator arm 62, some of the power of the excitation frequency from splitter 61 is transmitted to probe 14 via attenuator 82, pick-off tee 84, and band pass filter 86 before being split by splitter 26 and simultaneously transmitted through reference arm 22 and sample arm 24 as in the embodiment shown in FIG. 1. Here, shorting member 32 reflects the excitation frequency in the absence of sample 36 or at a non-resonant state of sample 36 and produces the signal frequency when sample 36 resonantly absorbs power from the excitation frequency. When the excitation frequency from reference arm 22 and sample arm 24 are present at combiner 38, reference arm 22 and sample arm 24 are balanced and the combined frequency that is output from combiner 38 has a low amplitude, perhaps zero. However, when sample 36 absorbs the excitation frequency, and the signal frequency is present at combiner 38, reference arm 22 and sample arm 24 are unbalanced. For the unbalanced case, the combined frequency output from combiner 38 is proportional to the number of unpaired electrons present in an excitation volume of shorting member 32 that absorb power from the excitation frequency. As mentioned, combiner 38 transmits the combined frequency to radiofrequency input 66 of mixer 64. Pick-off tee 76 can be interposed between amplifier 44 and mixer 64 to allow monitoring of the combined frequency.

Mixer 64 mixes the combined frequency at radiofrequency input 66 and the excitation frequency at local oscillator input 68 and produces a detection frequency (e.g., an intermediate frequency) at output port 70 of mixer 64. The detection frequency is transmitted subsequently to phase sensitive detector 48, which is locked to a phase and frequency of reference oscillator 50. In this arrangement, use of phase sensitive detector 48 to monitor the detection frequency at a frequency and phase of the reference frequency accomplishes heterodyne detection of the resonant absorption of the excitation frequency by sample 36 as a function of the excitation frequency and magnetic field strength. Therefore, in an embodiment, the electron spin resonance spectrometer includes the bridge that has the local oscillator arm, which includes the mixer, such that the bridge is configured to produce the detection frequency and to transmit the detection frequency to the detector.

The probe can be various types of probes that transmit the excitation frequency to the sample. Exemplary probes include a coaxial cable where the second conductor shields the first conductor (arranged as a central conductor in the cable), a strip line probe where the first conductor and the second conductor are metallic strips disposed on a substrate, and the like. For the probe, the first conductor and the second conductor are connected and electrically shorted together by the shorting member. As shown in FIG. 3, probe 90 is, e.g., a coaxial cable that has a terminus at first end 92 and second end 94. Dielectric material 100 is interposed between second conductor 98 that is surroundingly disposed about first conductor 96. Shorting member 102 electrically shorts first conductor 96 and second conductor 98. Joiner 104 optionally can be interposed between shorting member 102 and first conductor 96 and second conductor 98 to increase the contact and decrease a resistivity between shorting member 102 and conductors 96, 98. Joiner 104 is an electrically conductive material, e.g., a solder, a metal, an alloy, a conductive adhesive, and the like. Alternatively, shorting member 102 can be in direct physical contact with first conductor 96 and second conductor 98. Connector 106 can be present at second end 94 of probe 90. Connector 106 connects probe 90 to the bridge of the electron spin resonance spectrometer by, e.g., connection to the circulator of the sample arm of the bridge. According to an embodiment, probe 90 and the bridge are integrated into a monolithic structure with or without the presence of connector 106.

FIG. 4 shows a photograph of an end view at the terminus of first end 92 of probe 90. Second conductor 98 and first conductor 96 are arranged in a coaxial configuration and are shorted by shorting member 102 via joiner 104 and otherwise isolated from each other by dielectric material 100. Here, second conductor 98, first conductor 96, and shorting member 102 are copper, and joiner 104 is solder. Dielectric material 100 is polytetrafluoroethylene.

Although the electrical response of probe 90 having a coaxial arrangement of first conductor 96 and second conductor 98 is effective to transmit the excitation frequency with high fidelity, shorting member 110 constructed as a lumped circuit can be used in probe 108 as shown in a perspective view of such a shorting member in FIG. 5. In this embodiment, probe 108 includes first conductor 96 and second conductor 98 separated by dielectric material 100. Here, probe 108 includes shorting member 110, which is a lumped circuit. Shorting member 110 includes first conductor extension 112 connected to first conductor 96 and also second conductor extension 114 and auxiliary second conductor extension 114a connected to second conductor 98. Probe tip 116 electrically connects and short-circuits first conductor extension 112 to second conductor extension 114. First conductor extension 112, second conductor extension 114, and auxiliary second conductor extension 114a are disposed on basal member 118 and extend substantially parallel to one another. Auxiliary second conductor extension 114a is included so that shorting member 110 has similar electrical characteristics (e.g., impedance, capacitance, and the like) as the coaxial portion of probe 108 that includes first conductor 96 coaxial to second conductor 98.

Figure 6:
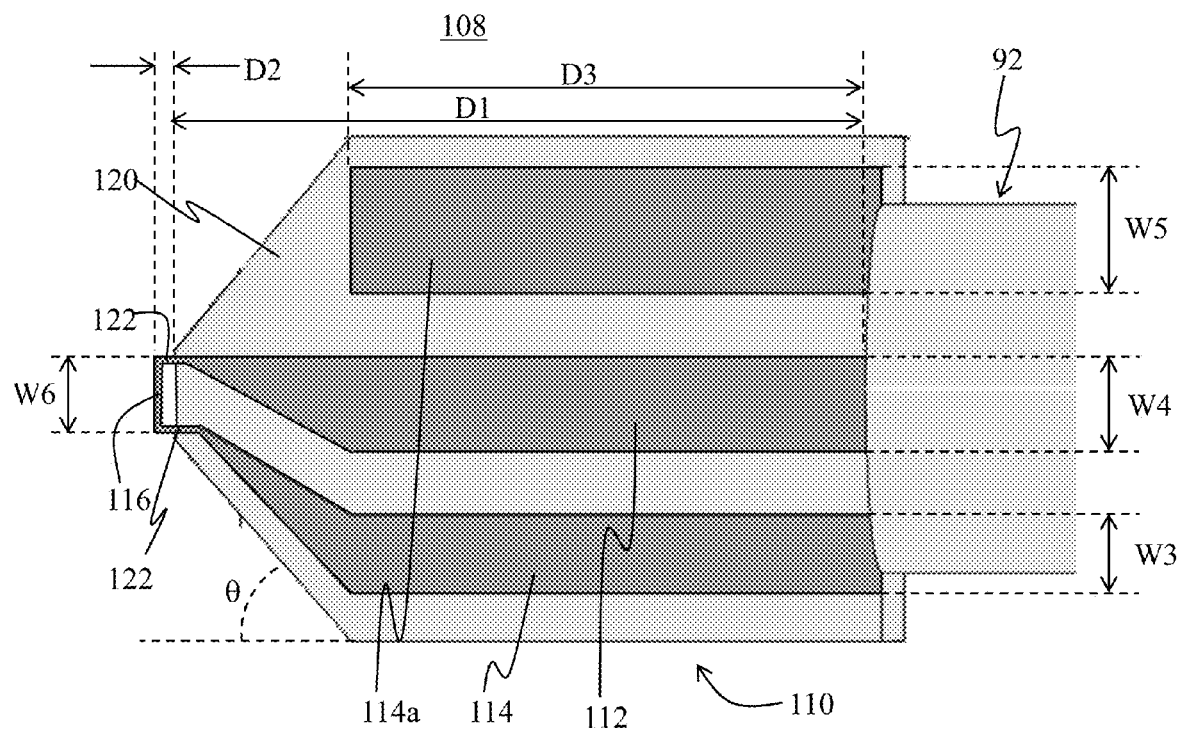
FIG. 6 shows a top view of the probe shown in FIG. 5.
Figure 7:
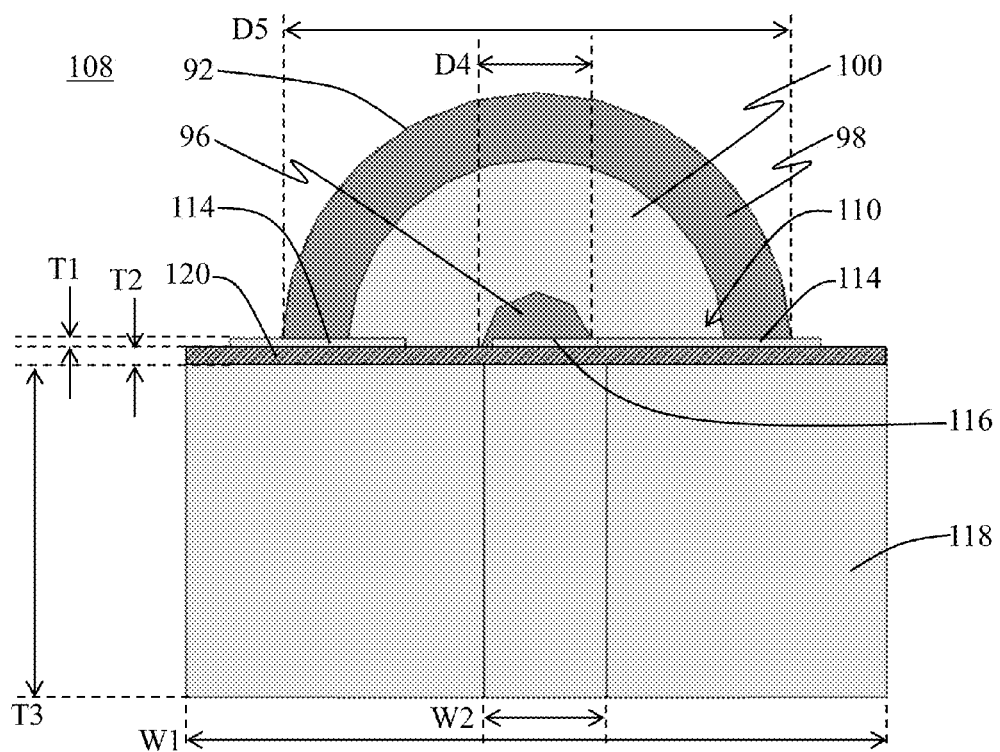
FIG. 7 shows an end view of the probe shown in FIG. 5.

Nonconductive layer 120 can be interposed between basal member 118 and first conductor extension 112, second conductor extension 114, or auxiliary second conductor extension 114a. Additionally, as shown in a top view of probe 108 in FIG. 6 and the end view of probe 108 in FIG. 7, protrusion 122 connects probe tip 116 to first conductor extension 112 and second conductor extension 114 such that probe tip 116 is separated from basal member 118 by distance D2. Moreover, first conductor extension 112 and second conductor extension 114 independently have length D1 and respective widths W3 and W4. Auxiliary second conductor extension 114a has length D3 and width W5. First conductor extension 112, second conductor extension 114, and auxiliary second conductor extension 114 have thickness T1, and the thickness of nonconductive layer 120 and basal member 118 are respectively T2 and T3. A width of basal member 118 is W1. Basal member 118 proximate to probe tip 116 tapers from width W1 to width W2 at an angle θ (shown in FIG. 6). In this manner, probe tip 116 can be very compact, e.g., having a size (width W6 or thickness T1) on the nanometer scale using nanotechnology fabrication technology such as nanolithography, etching, atomic beam deposition, and the like to form a structure of shorting member 108. A nano- or micron-sized probe tip 116 provides high spatial resolution to spectroscopically probe samples on an atomic-scale.

According to an embodiment, the electron spin resonance spectrometer includes the shorting member that is arranged as the lumped circuit. The shorting member includes the first conductor extension electrically connected to the first conductor, the second conductor extension electrically connected to the second conductor, and the probe tip electrically shorting the first conductor to the second conductor such that the probe tip is configured to transmit the excitation frequency to the sample. Here, the shorting member further includes the basal member such that the first conductor extension and the second conductor extension are disposed on the basal member, and the probe tip extends from the first conductor extension and the second conductor extension such that a portion of the probe tip is not disposed on the basal member. The portion of the shorting member that transmits the excitation frequency to the sample is disposed external to the magnet. Moreover, the shorting member is disposed at the first end of the probe, and the connector is disposed at the second end of the probe such that the connector is configured to electrically connect the probe to the bridge. In some embodiments, the connector is not present, but the probe is integrally part of the bridge in a monolithic structure.

Figure 8:
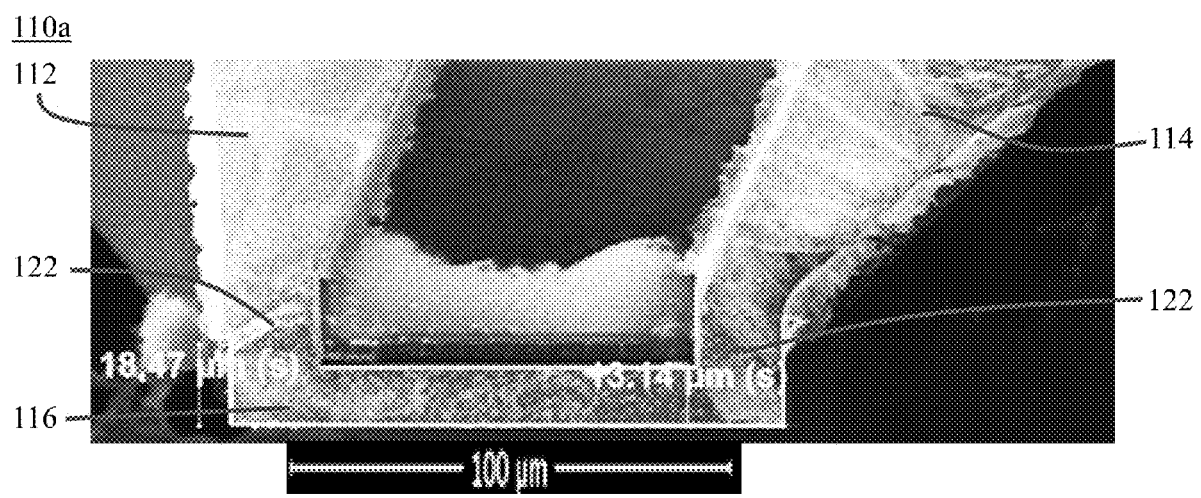
FIG. 8 shows a micrograph of a shorting member.
Figure 9:
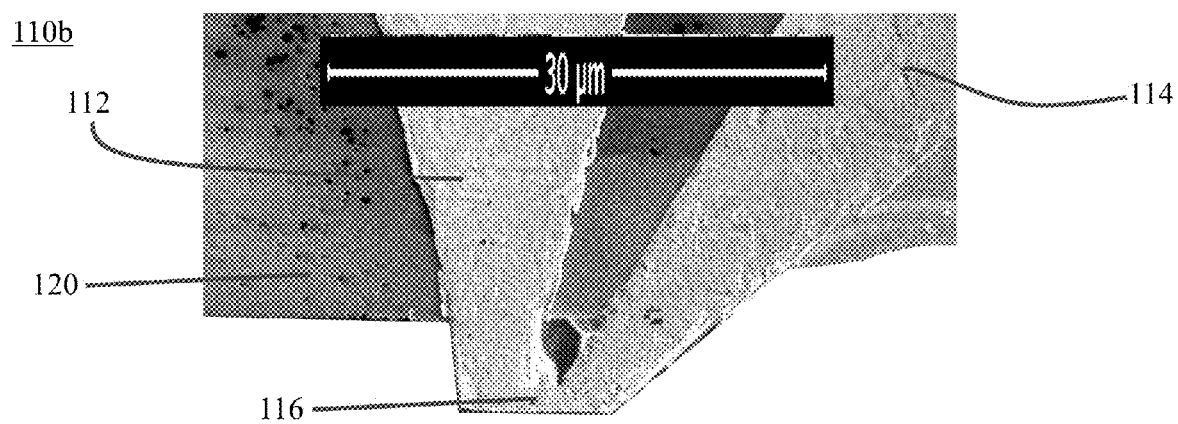
FIG. 9 shows a micrograph of a shorting member.
Figure 10:
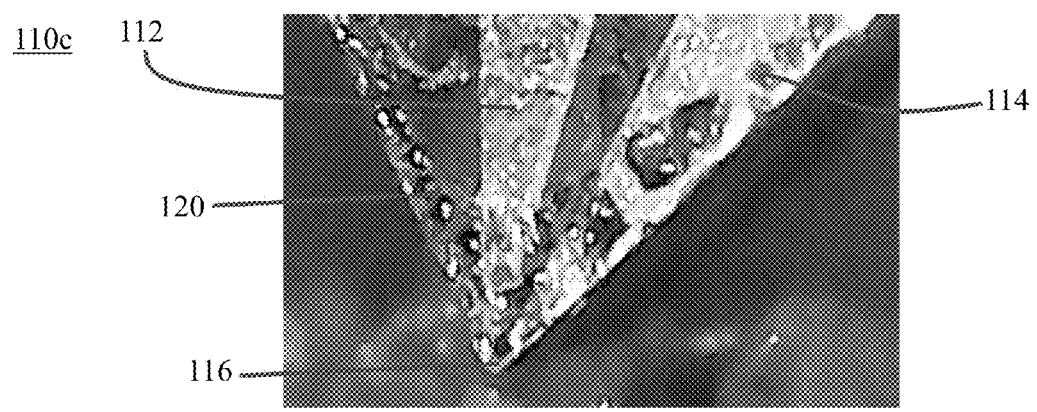
FIG. 10 shows a photograph of a shorting member.

FIGS. 8 and 9 show micrographs acquired from scanning electron microscopy of two different shorting members 110a and 110b, which respectively have probe tip lengths of 80 µm and 2 µm. Shorting member 110c shown in the optical microscope photograph in FIG. 10 has pointed probe tip 116 of approximately 2 µm in the horizontal direction.

Figure 11:
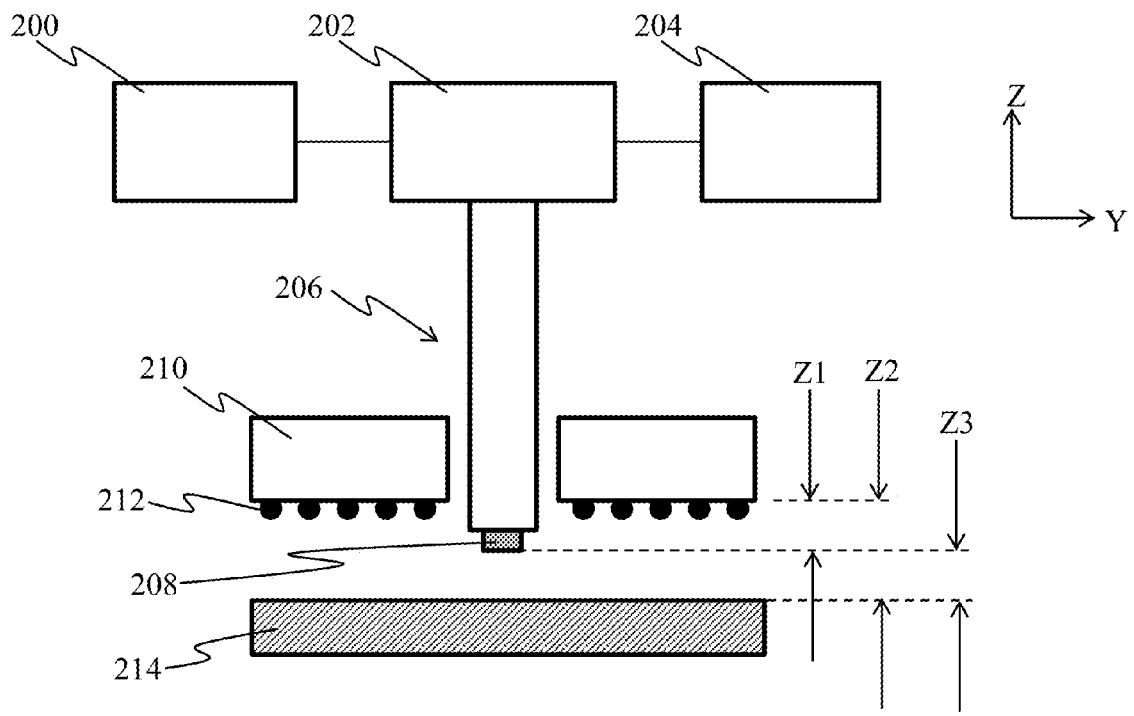
FIG. 11 shows an electron spin resonance spectrometer arranged with a magnet concentrically disposed around a probe.

The relative position of the magnet, the probe, and the sample can be selected, e.g., to account for sample geometry, a physical property of the sample, a chemical property of the sample, and the like. In some embodiments, as shown in FIG. 11, an electron spin resonance spectrometer is arranged such that bridge 202 interconnects an excitation source 200, probe 206, and detector 204. Shorting member 208 is disposed at a terminus of probe 206 with magnet 210 disposed around probe 206 such that probe tip 208 extends beyond modulation coil 212 disposed on a surface of magnet 210. Here, sample 214 is opposingly disposed external to probe 206, magnet 210, and modulation coil 212. The positive Z- and Y-axes are indicated as an inset in FIG. 11, with the positive X-axis projecting orthogonally outward from the plane of FIG. 11. A distance between magnet 210 and probe tip 208 is Z1, between magnet 210 and proximate surface of sample 214 is Z2, and between probe tip 208 and proximate surface of sample 214 is Z3.

Figure 12:
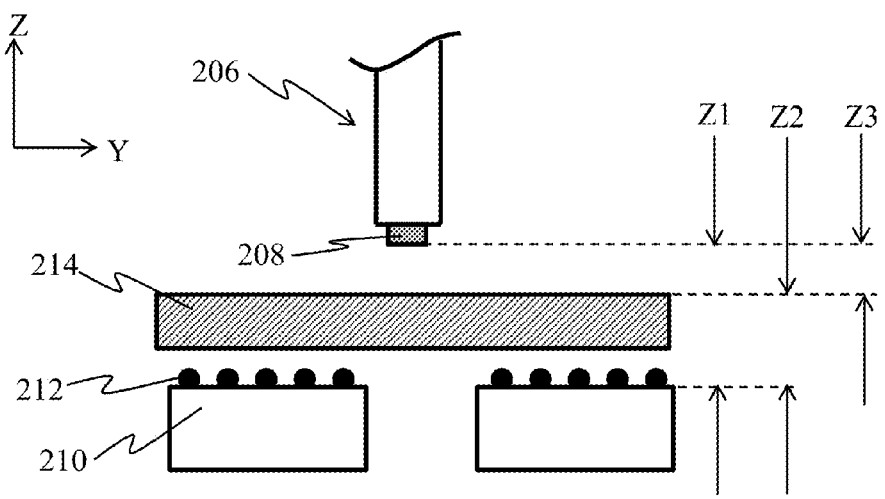
FIG. 12 shows an electron spin resonance spectrometer arranged with a sample interposed between a magnet and a probe.

Although the magnet is surroundingly disposed around the probe in some embodiments, in other embodiments magnet 210 is opposingly disposed to shorting member 208 such that sample 214 is interposed between probe 206 and modulation coil 212 as in FIG. 12. Here, the distances between magnet 210 and probe tip 208 is Z1, between magnet 210 and the surface of sample 214 proximate to probe tip is Z2, and between probe tip 208 and the proximate surface of sample 214 is Z3. According to an embodiment, sample 214 is interposed between and external to magnet 210 (with modulation coil 212) and probe tip 208 of probe 206.

Figure 13:
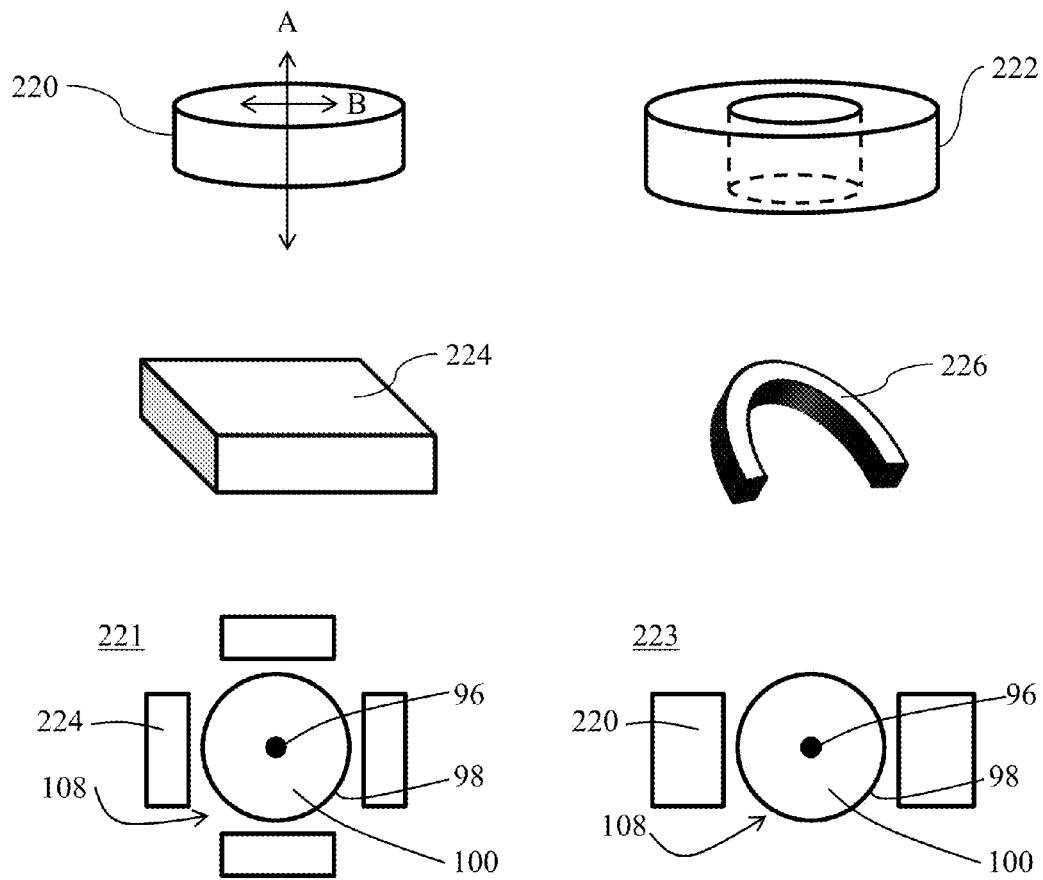
FIG. 13 shows a plurality of magnets for disposal proximate to an electron spin resonance spectrometer probe.

The magnet can be a monolithic structure or a plurality of pole pieces, and the magnet or pole pieces thereof can have a variety of shapes, e.g., as in FIG. 13, cylindrical shape 220, annular shape 222, bar shape 224, semi-annular shape (e.g., a horse shoe shape) 226, and the like. The magnetic poles of the magnet can be oriented parallel to a major axis A of the magnet (typically an axis of highest symmetry) or a minor axis B (see orthogonal axes A and B superimposed on magnet 220). Furthermore, for a magnet having cylindrical symmetry such as cylindrical magnet 220 or annular magnet 222, the magnetic poles may be oriented radially from the axis of symmetry. According to an embodiment, the magnet is an annular magnet 222 surroundingly disposed around the probe (see FIG. 15). In some embodiments, the magnet is a bar magnet 224 disposed opposing the probe such that a sample is interposed between bar magnet 224 and the probe. In a particular embodiment, a plurality of magnets are disposed proximate to the probe, e.g., a plurality of bar magnets 224 are disposed equidistantly around probe 108 as shown for a transverse cross section 221 of probe 108 having first conductor 96, second conductor 98 coaxially disposed around the first conductor, and dielectric material 100 interposed therebetween.

It is contemplated that an orientation of the magnet with respect to the probe can be selected such that a major axis A of the magnet can make any desired angle with the long axis (Z-axis in FIGS. 11 and 12) of probe 206. According to an embodiment, a plurality of cylindrical magnets 220 are disposed about probe 108 as shown for a transverse cross-section 223 of probe 108 such that each cylindrical magnet 220 has its major axis A orthogonal to and radially pointing to the long axis Z of probe 108.

Figure 14:
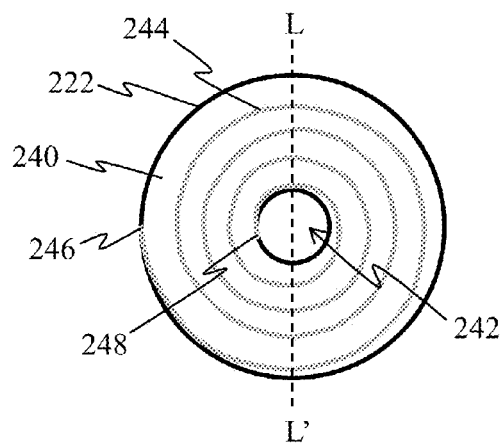
FIG. 14 shows an end view of a magnet with a modulation coil disposed on a surface of the magnet.
Figure 15:
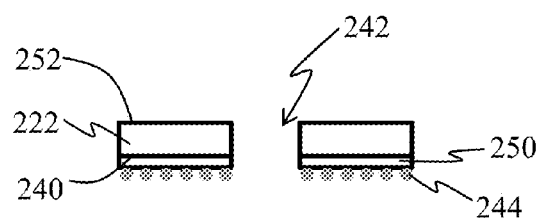
FIG. 15 shows a cross-sectional view of the magnet of FIG. 14.

The magnet provides a magnetic field to the sample as above discussed. The modulation coil is disposed on a surface of the magnet such that the modulation coil is disposed entirely or partially between the magnet and the sample. The modulation coil can have a variety of shapes provided that the shape is consistent with the modulation coil modifying the magnetic field from the magnet that is applied to the sample. As shown in FIG. 14, in an embodiment, a bottom view of annular magnet 222 has first surface 240 and bore 242 with modulation coil 244 in a spiral arrangement disposed on first surface 240. Modulation coil 244 includes first end 246 and second end 248 to electrically connect, modulation coil 244 to the bias tee (e.g., bias tee 56, FIGS. 1 and 2) so that the reference frequency and the bias voltage can be applied to modulation coil 244. A transverse cross-section of annular magnet 222 along L-L' is shown in FIG. 15, where modulation coil 244 is optionally separated from annular magnet 222 by spacer 250 that is disposed on first surface 240 opposing second surface 252 of annular magnet 222. In an embodiment, spacer 250 is a heat sink or a temperature regulator for annular magnet 222 or modulation coil 244. Spacer 250 can include an electrically conductive material (e.g., a metal, a polymer, and the like) or an electrically insulating material (e.g., a ceramic, a glass, a polymer, and the like). Spacer 250 can have a magnetic permeability of free space such that spacer 250 does not alter the magnetic field from the magnet. Alternatively, spacer 250 can have a magnetic permeability such that spacer 250 can deform a shape of the magnetic field from the magnet. It is contemplated that a heat sink thermally contacts the magnet, the probe, or a combination comprising at least one of the foregoing. Additionally, in some embodiments, a temperature regulator is connected to a component of the electron spin resonance spectrometer to regulate a temperature of the magnet, the probe, or a combination comprising at least one of the foregoing. The heat sink or temperature regulator can be a heat exchanger, a Peltier junction, a thermoelectric device, and the like. The heat sink or temperature regulator can be thermostatically controlled.

The materials used in construction of the electron spin resonance spectrometer can be selected based on, e.g., an operational parameter of the spectrometer such as efficient transmission of the excitation frequency, signal frequency, combined frequency, detection frequency; a size of the electron spin resonance spectrometer, an excitation volume, a sample; a frequency of a transmitted frequency; and the like. For the probe, the first conductor, the second conductor, the shorting member, the probe tip, the protrusion, the first conductor extension, and the second conductor extension independently include a metal such as aluminum, chromium, copper, gold, molybdenum, silver, tantalum, tungsten, an alloy thereof, or a combination comprising at least one of the foregoing. Further, in the lumped circuit arrangement of the shorting member, the first conductor extension, the second conductor extension, the auxiliary second conductor extension, or the probe tip independently can be formed in a laminate structure containing a plurality of layers, e.g., a base layer of tungsten coated with an overlayer of gold. The cross-sectional shape of a lumped circuit element of the shorting member, e.g., the probe tip, can have a shape effective to transmit at the frequency of the excitation frequency or signal frequency such as a round shape, elliptical shape, square shape, rectangular shape, and the like. In some embodiments, the second conductor is disposed as an external surface of the probe in a coaxial arrangement with the first conductor. In an embodiment, an electrical insulator, e.g., polyethylene, polytetrafluoroethylene, polyvinylchloride, and the like, surrounds the second conductor. In a particular embodiment, the probe is rigid. In another embodiment, the probe is flexible.

The electron spin resonance spectrometer is scalable in size (e.g., to accommodate various samples) and operates over a wide frequency range (e.g., in the megahertz (MHz) or gigahertz (GHz) frequencies). Moreover, the electron spin resonance spectrometer does not include a cavity so that a size of a cavity or a resonant condition of a cavity does not constrain the electron spin resonance spectrometer herein in size, construction, configuration, excitation frequency, and the like. In this regard, the probe can be various sizes. A total length of the probe can be selected to access a sample at a selected distance from the bridge, e.g., from several micrometers to several meters. In an embodiment, the probe has a length from 10 µm to 10 m, specifically 100 µm to 1 m, and more specifically 10 cm to 50 cm.

With reference again to FIGS. 6 and 7, first conductor 96 can have a diameter D4 from several nanometers to several centimeters, e.g., from 200 nm to 2 cm, specifically 1 µm to 1 mm, and more specifically 100 µm to 500 µm. Second conductor 98 can be externally and coaxially disposed to first conductor 96 and can have an inner diameter that is radially separated from an outer surface of first conductor 96 by a distance effective so that the excitation frequency is efficiently reflected to the circulator from shorting member 108 without interference from an external radiation frequency or without electrical breakdown or power leakage between first conductor 96 and second conductor 98. Further, a wall thickness of second conductor 98 can be in the micrometer or millimeter range, e.g., less than 2 mm, less than 1 mm, less than 500 µm, and the like. An outer diameter D5 of second conductor 98 can be any size such as, e.g., from 1 µm to 10 cm, specifically 10 µm to 10 mm, and more specifically 500 µm to 1 mm.

First conductor extension 112, second conductor extension 114, and auxiliary second conductor extension 114a can be the same size or independently can have width (W3, W5, W5), e.g., from 300 nm to 2 cm, specifically 2 µm to 2 mm, and more specifically 150 µm to 750 µm; length (D1, D3), e.g., from 10 nm to 10 cm, specifically 100 µm to 1 cm, and more specifically 500 µm to 1 mm; and thickness (T1) from 10 nm to 1 mm, specifically 1 µm to 100 µm, and more specifically 5 µm to 10 µm. As indicated previously, extensions (112, 114, 114a) independently can have a laminate structure. Each layer of the laminate structure can be the same thickness or a different thickness. In an embodiment, extension (112, 114, or 114a) has the laminate structure and includes a plurality of layers such as a first metal layer (e.g., tungsten and the like) and a second metal layer (e.g., gold and the like) disposed on the first metal layer such that the first metal layer has a greater thickness than the second metal layer.

Dielectric material 100 separates and electrically insulates first conductor 96 from second conductor 98 over the range of frequency and power of the excitation frequency. Dielectric material 100 can have a dielectric strength effective for electrically insulating first conductor 96 from second conductor 98. Exemplary dielectric materials include a ceramic, a polymer, a glass, and the like. In an embodiment, dielectric material 100 has a dielectric strength greater than or equal to from 100 kilovolts per centimeter (kV/cm) to 10 megavolts (MV)/cm at an excitation frequency effective to excite an electron spin transition in the sample.

In shorting member 108, probe tip 116 and protrusions 122 can have a same or different size as extensions (112, 114) to which they connect. Furthermore, width W6 and thickness T1 of probe tip 116 and protrusions 122 independently can be from 1 nm to 1 cm, specifically 1 µm to 1 mm, and more specifically 10 µm to 100 µm. In an embodiment, a length of the probe tip that is configured to transmit the excitation frequency to the sample has a length from 500 nm to 500 µm.

Basal member 118 on which extensions (112, 114, 114a) are disposed can include a material that is electrically nonconductive or has a resistivity that is much greater than that of probe tip 116 such that the excitation frequency and signal frequency are transmitted through electrically conductive probe tip 116, protrusions 122, and extensions (112, 114, 114a) instead of through basal member 118. In an embodiment, basal member 118 includes a polymer (e.g., polytetrafluoroethylene, polyethylene, polypropylene, propylene, polyimide, polyamideimide, and the like), a ceramic, aluminum nitride, boron nitride (BN), aluminum oxide ($Al_2O_3$), beryllium oxide (BeO), SiO, $SiO_2$, $Si_3N_4$, $Ta_2O_5$, glass, quartz, sapphire, silicon, gallium arsenide, or a combination comprising at least one of the foregoing. In a specific embodiment, basal member 118 is a silicon chip.

According to an embodiment, nonconductive layer 120 interposed between basal member 118 and extensions (112, 114, 114a) is an electrically insulating or dielectric material such as a ceramic, aluminum nitride, boron nitride (BN), $Al_2O_3$, BeO, SiO, $SiO_2$, $Si_3N_4$, $Ta_2O_5$, glass, quartz, sapphire, silicon, gallium arsenide, and the like. In one embodiment, nonconductive layer 120 is silicon nitride.

Proximate to the probe is the magnet. The magnet can be a permanent magnet, an electromagnet, a superconducting magnet, or a combination thereof. According to an embodiment, the magnet is a permanent magnet that includes an element such as aluminum, iron, nickel, cobalt, a rare earth metal, and the like. Exemplary magnets include an R—Fe—B magnet (where R is a rare earth element, e.g., Y, Sc, La, Ce, Pr, Nd, Sm, Eu, Gd, Tb, Dy, Ho, Er, Yb, and Lu), specifically a Nd—Fe—B (e.g., $Nd_2Fe_{14}B$) magnet, a Sm—Co magnet, and the like. The magnet may include additional elements (e.g., Al, Cu, Zn, In, Si, P, S, Ti, V, Cr, Mn, Ni, Ga, Ge, Zr, Nb, Mo, Pd, Ag, Cd, Sn, Sb, Hf, Ta, or W) in various amounts to achieve a selected magnetic field strength or permeability.

Connected to the probe is the bridge that interconnects the probe to the source and the detector. In an embodiment, as shown in FIGS. 1 and 2, the bridge can include a combination of elements such as a splitter, combiner, attenuator, phase shifter, circulator, amplifier, mixer, pick-off tee, filter, and the like. Moreover, an element can be a variable output element such as variable attenuator or variable phase shifter. An additional component such as a switch (e.g., a diode switch), isolator, waveguide, power meter, directional coupler, and the like can be connected to the bridge, source, or detector via, e.g., a coaxial cable to efficiently transmit the various frequencies (e.g., the excitation frequency, signal frequency, and the like). The excitation source connected to the bridge provides the excitation frequency and can be a device that produces an electromagnetic wave in the megahertz or gigahertz frequency range. Exemplary excitation sources include a klystron, a frequency synthesizer, a backward wave oscillator, and the like. Similarly, the reference oscillator can be a solid state oscillator. As indicated above, the detector is a phase sensitive detector, e.g., a lock-in amplifier, having a modulated signal (e.g., combined frequency, detector frequency, and the like) as an input referenced to, e.g., the reference frequency. In an embodiment, the lock-in amplifier can produce the reference frequency so an output of the lock-in amplifier connects to the modulation coil to modify the magnetic field applied to the sample. Additional components of the electron spin resonance spectrometer include the reference oscillator, which can be a crystal oscillator source, a frequency synthesizer, a function generator and the like. Similarly, the power source for supplying the bias voltage can be, e.g., a sweep generator and the like.

An electron spin resonance spectrometer in accordance with an embodiment subjects the sample to the excitation frequency and provides spectroscopic information based on the signal frequency. Typically, the spectroscopic information is an electron spin resonance spectrum but is not limited thereto. In some embodiments, an electron spin resonance signal at a particular electron spin resonance frequency is acquired without acquisition of further spectral information such as non-peak absorption electron spin resonance data. According to an embodiment, a method for acquiring an electron spin resonance spectrum includes disposing a sample in an electron spin resonance spectrometer that includes a bridge, which includes a sample arm and a reference arm, a probe electrically connected to the bridge, a detector electrically connected to the bridge, a magnet disposed proximate to the probe and the sample, and a modulation coil interposed between the magnet and the sample. The probe includes, e.g., a first conductor electrically connected to the bridge, a shorting member electrically connected to the first conductor, and a second conductor electrically connected to the shorting member. The method further includes transmitting an excitation frequency from an excitation source to the sample through the sample arm and the shorting member, modulating a magnetic field present at the sample from the magnet at a reference frequency applied to the modulation coil, absorbing (by the sample) the excitation frequency, producing a signal frequency at the shorting member, transmitting the signal frequency from the shorting member toward the detector, combining the signal frequency from the sample arm and the excitation frequency from the reference arm to produce a detection frequency, and detecting (by the detector) the detection frequency as a function of changing the excitation frequency or a magnetic field strength present at the sample to acquire the electron spin resonance spectrum. It is contemplated that the sample is disposed external to the probe, the magnet, and the modulation coil. In this manner, the electron spin resonance spectrum is acquired from the sample proximate to the probe and subjected to a variation in the excitation frequency, the applied magnetic field, or a combination thereof. Accordingly, the electron spin resonance spectrometer is configured to acquire an electron spin resonance spectrum in response to varying the excitation frequency present at the shorting member, a magnetic field strength applied to the sample from the magnet, or a combination comprising at least one of the foregoing.

Figure 16:
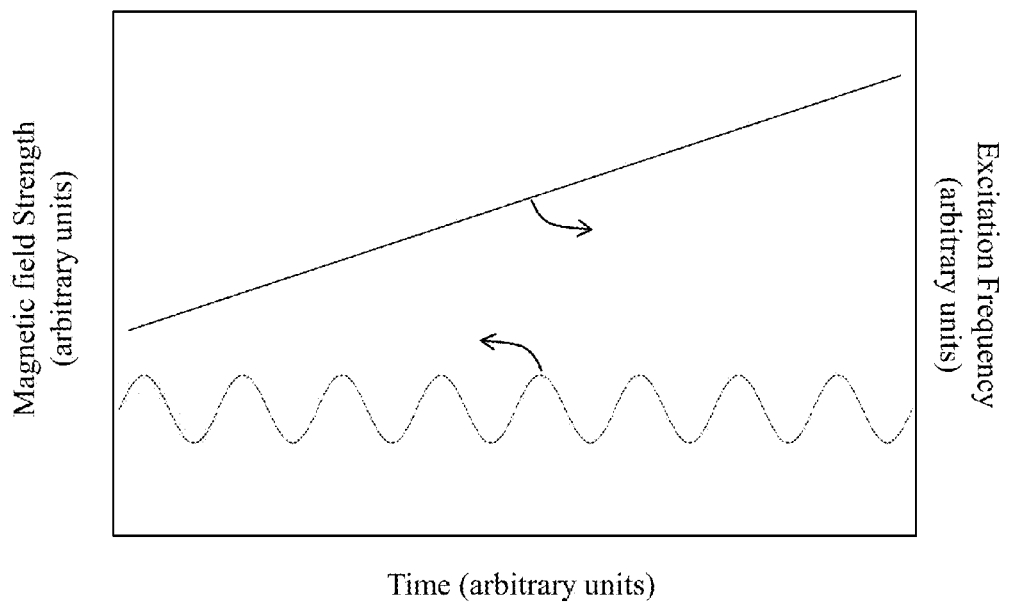
FIGS. 16 and 17 show a graph of magnetic field strength and excitation frequency versus time.

In an embodiment, the electron spin resonance spectrum is acquired by fixing the magnetic field strength applied to the sample from the magnet while scanning the excitation frequency, which can be accomplished, e.g., by adjusting an output frequency of the excitation source. Here, the magnetic field applied to the sample can be modulated at the reference frequency (from, e.g., reference oscillator 50, FIG. 1) at a constant bias voltage from the power source (e.g., power source 54, FIG. 1), as depicted in FIG. 16, which shows the modulation of the magnetic field strength applied to the sample at a constant bias voltage level (the lower curve associated with the left-hand y-axis) while varying the excitation frequency (the upper curve associated with the right-hand y-axis).

While the magnet provides a magnetic field having a certain magnetic field strength at the sample, the magnetic field strength applied to the sample is modified by the bias voltage applied to the modulation coil. Since the bias voltage is applied to the modulation coil as current flows through the modulation coil, the flow of the current in the modulation coil establishes a secondary magnetic field perpendicular to the direction of electron movement through the modulation coil. Increasing an amount of the current through the modulation coil, increases the strength of the secondary magnetic field produced by modulation coil. Reversing the direction of the current through the modulation coil reverses the direction of the secondary magnetic field produced by the modulation coil. A variation in a direction or strength of the secondary magnetic field modifies the magnetic field from the magnet. Therefore, the magnetic field applied to the sample is modulated due to the variation of the secondary magnetic field produced by the modulation coil.

Figure 17:
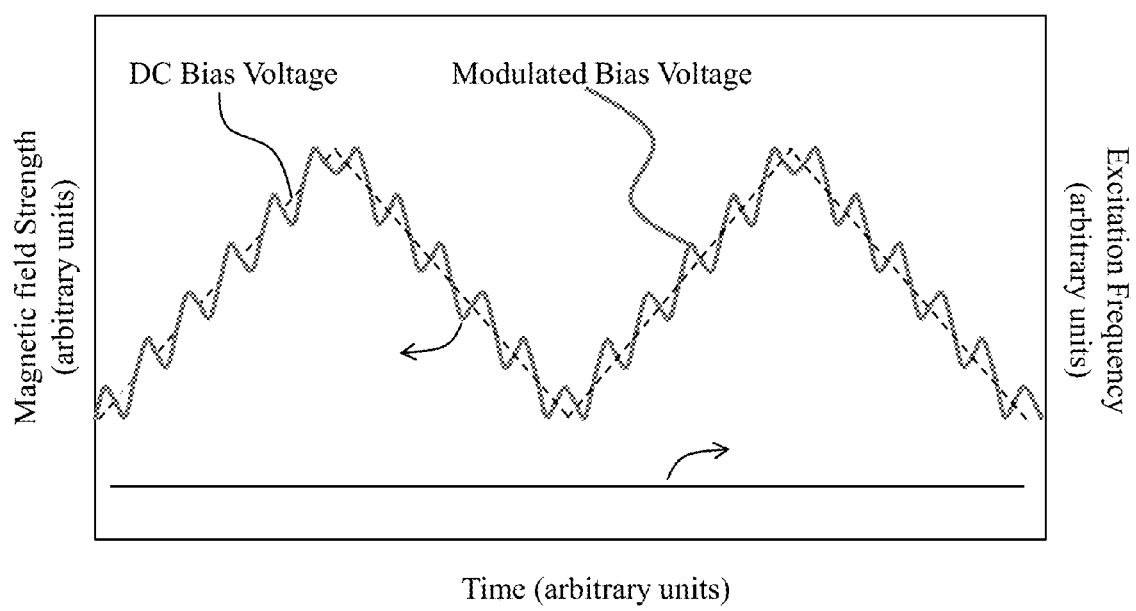

According to an embodiment, as shown in FIG. 17, the electron spin resonance spectrum is acquired by fixing the excitation frequency (the lower curve associated with the right-hand y-axis) while scanning the magnetic field strength (the upper curve associated with the left-hand y-axis) applied to the sample. This can be accomplished, e.g., by maintaining the output frequency of the excitation source at a selected value while the magnetic field strength applied to the sample is modulated at the reference frequency of the reference oscillator and temporally scanning the level of the bias voltage from the power source (e.g., power source 54, FIG. 1). That is, a direct current (DC) bias voltage that is applied to the modulation coil from power source 54 is swept while the reference frequency from reference oscillator 50 (FIG. 1) also is applied to the modulation coil. The DC bias voltage is shown as a dashed upper curve in FIG. 17, and the overall modulated bias voltage (modulated at the reference frequency) that is applied to the modulation coil is the solid upper curve superimposed on the DC bias voltage.

Thus, the sample is subjected to the magnetic field applied from the combination of the magnet and the modulation coil. This magnetic field is modulated at the reference frequency and causes any unpaired electrons in the sample to experience a Zeeman splitting into a plurality of nondegenerate states having a frequency separation that depends on the strength of the applied magnetic field. In addition, the probe tip receives the excitation frequency and subjects the sample to the excitation frequency for a portion of the sample that is within an excitation volume of the probe tip. The excitation volume is determined, e.g., by the geometry or size of the probe tip. Thus, the sample is subjected to an oscillating electric field and magnetic field from the excitation frequency at the probe tip in addition to the applied magnetic field from the combination of the magnet and the modulation coil. When the excitation frequency satisfies a resonant absorption condition of the unpaired electrons (i.e., the excitation frequency is resonant with the Zeeman splitting among the nondegenerate states), the sample absorbs some of the power from the excitation frequency to generate a signal frequency at the probe tip. Since the Zeeman splitting of the plurality of nondegenerate states is modulated at the reference frequency, absorption is modulated at the reference frequency. As a result, the signal frequency is modulated as a superposition of the reference frequency and the excitation frequency.

Figure 18:
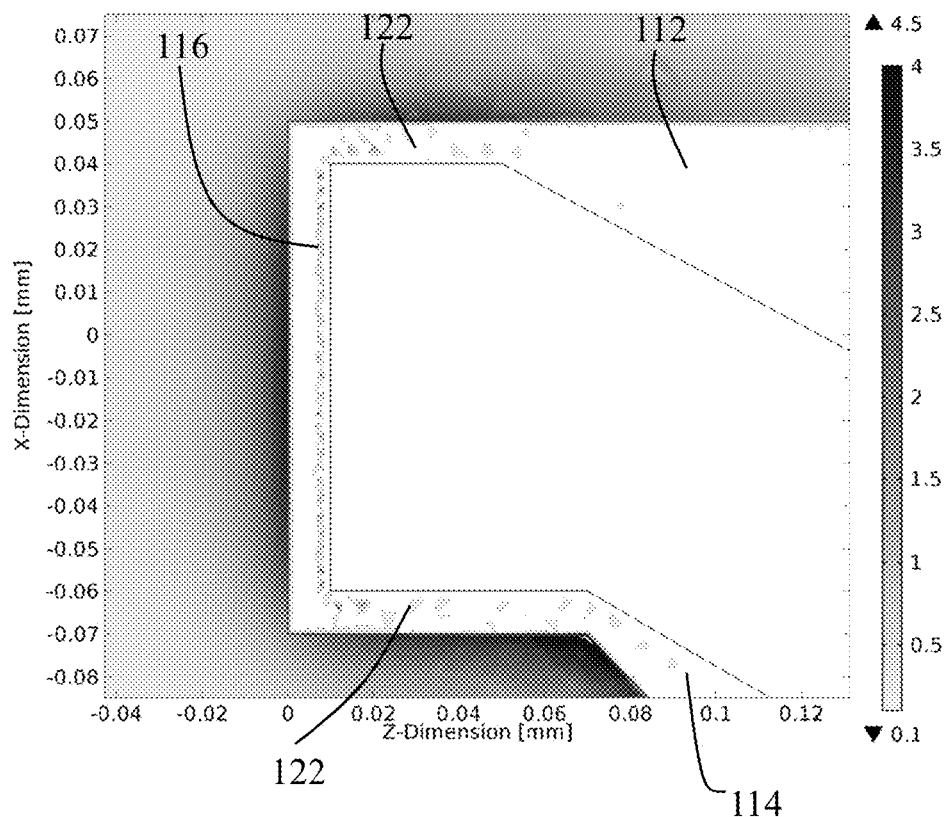
FIG. 18 shows a plot of magnetic field flux density for a shorting member provided with an excitation frequency.

In an embodiment, the electron spin resonance spectrometer herein selectively and spatially detects unpaired electrons in the sample. As shown in FIG. 18, a cross-section of a terminus of a probe is superimposed on a graph of a magnetic field flux density (units of Gauss, G) for x- and y-coordinates of the probe. The probe has probe tip 116 that electrically short-circuits and connects, via protrusions 122, first conductor 112 and second conductor 114. A magnitude and phase of the magnetic field flux density are provided in the legend bar to the right of the graph. These data are simulated from an input excitation frequency having an input voltage amplitude of 0.5 volts and a phase of $2\pi/3$ radians at room temperature and atmospheric pressure. The magnetic field flux density is stable and uniform over probe tip 116 where the sample is subjected to the excitation frequency from the probe tip such that absorption at an electron spin resonance frequency is localized within the excitation volume near the probe tip. Here, the magnetic field near probe tip 116 is about 4 G, which is great enough for absorption of the excitation frequency by unpaired electrons in a sample. Thus, the electron spin resonance spectrometer is an absorption spectrometer.

As indicated above, in an embodiment, the excitation frequency is scanned to produce the electron spin resonance spectrum. In other embodiments, the excitation frequency is kept constant, and the applied magnetic field strength is scanned to acquire the spectrum. According to some embodiments, the excitation frequency is modulated before being transmitted to the probe tip. Exemplary modulations of the excitation frequency include frequency modulation (FM), amplitude modulation (AM), phase modulation, and the like. Furthermore, the excitation frequency can be continuous wave or pulsed. Since the probe is not disposed in a cavity, the excitation frequency can be pulsed, and the signal frequency subject to detection without any delay between the pulse of the excitation frequency and providing the detection frequency to the detector. According to an embodiment, the electron spin resonance spectrometer is operated with a pulsed excitation frequency without a delay between production of the signal frequency at the probe tip and detection of the detection frequency because the signal frequency can be converted to the detection frequency at any point during a free induction decay of the absorption of the excitation frequency at the sample. Moreover, the electron spin resonance spectrometer is configured to acquire the electron spin resonance spectrum without changing a dimension of a cavity over an entire range of the excitation frequency and the magnetic field strength applied to the sample.

In the electron spin resonance spectrometer, various frequencies (e.g., the excitation frequency, the signal frequency, the combined frequency, the detection frequency, the reference frequency, and the like) can be present. The excitation frequency is selected to excite resonantly a spin of any unpaired electron in the sample. As such, the excitation frequency can be from 1 megahertz (MHz) to 300 gigahertz (GHz), specifically from 100 MHz to 100 GHz, and more specifically from 1 GHz to 30 GHz. In addition, the excitation frequency can be scanned over the entire aforementioned range, inclusive of each frequency within the range such that the electron spin resonance spectrometer is configured to acquire the electron spin resonance spectrum with the excitation frequency from, e.g., 1 MHz to 100 GHz, inclusive of each excitation frequency. Further, in an embodiment, the reference frequency applied to the modulation coil has a frequency that is less than that of the excitation frequency such that, for absorption by the sample, the reference frequency is a carrier wave for reflected, unabsorbed excitation frequency power within the signal frequency. The reference frequency is, e.g., from 1 hertz (Hz) to 1 GHz, specifically 100 Hz to 100 MHz more specifically from 1 kHz to 100 kHz. In an embodiment, the reference frequency is 100 kilohertz (kHz).

A power of the excitation frequency can be selected to be effective to cause resonant absorption of the unpaired electron in the sample, e.g., from 100 femtowatts (fW) to 100 W, specifically from 3 µW to 3 W, and more specifically from 1 mW to 100 mW. According to an embodiment, the power of the excitation frequency is from 1 mW to 100 mW in the continuous wave mode. In the pulsed mode, the excitation frequency can be selected in view of a duty cycle of the pulsed excitation frequency. It is contemplated that the peak power during pulsed mode operation is from 1 picowatts (pW) to 20 kilowatts (kW), specifically from 1 µW to 100 W, and more specifically from 1 watts (W) to 10 W at a pulse width duration from 20 ps to 100 µs, specifically from 1 ns to 10 µs, and more specifically from 20 ns to 500 ns with a repetition rate from 1 Hz to 1 MHz. In an embodiment, the duty cycle is 50% in pulsed mode operation of the excitation frequency.

The electron spin resonance spectrometer also includes a plurality of devices that are inserted along a transmission pathway of the various frequencies (e.g., the excitation frequency, the signal frequency, the combined frequency, the detection frequency, the reference frequency, and the like) that are present. Exemplary devices include attenuators (variable or fixed), combiners, splitters, amplifiers, band pass filters, switches, pick-off tees, and the like. These devices can reduce (e.g., for an attenuator) a power of an input frequency to the device by, e.g., 0 decibels (dB) to 100 dB or can increase (e.g., for an amplifier) the power of an input frequency by, e.g., 0 dB to 100 db.

As previously described, the excitation frequency is incident at the probe tip disposed proximate to the sample, and a magnetic field is applied to the sample. The magnetic field experienced by the sample is a combination of the magnetic fields of the magnet and the modulation coil. The magnet can have a field strength from 350 microTesla (µT) to 11 T, specifically from 3 mT to 4 T, and more specifically from 35 mT to 1 T. In addition, a magnitude of the strength of the magnetic field produced by the modulation coil can be from 0 T to 50 mT, specifically from 10 µT to 35 mT, and more specifically from 100 µT to 1 mT at the aforementioned reference frequency. Consequently, the strength of the magnetic field applied to the sample can be from 0 T to 11 T, specifically from 3.5 mT to 3.5 T, and more specifically from 35 mT to 1 T.

The electron spin resonance spectrometer herein has numerous beneficial advantages including high sensitivity, high resolution, fast acquisition speed, or low noise without limiting the size or geometry of the sample. Moreover, the electron spin resonance spectrometer can be miniaturized or can be portable. Additionally, the probe can be compact in size to fit in a constrained space. Furthermore, the probe works with a sample of any shape or geometry because the probe tip can be small relative to the sample size. A large probe tip can be included in the probe to provide a relatively large excitation volume without loss of sensitivity or diminution in response to signal frequency generation due to sample absorption at the excitation frequency. Advantageously, the electron spin resonance spectrometer is configured without a cavity so that the excitation frequency does not depend on any characteristic of a cavity. As such, the probe is configured to transmit energy and not to store energy. Therefore, in an embodiment, the electron spin resonance spectrometer has a quality factor (Q-factor) that is essentially unity, i.e., $Q \approx 1$, specifically less than or equal to 2 and more specifically less than or equal to 1.

In a beneficial arrangement, the probe is a near-field probe that can be stationary with respect to the sample or can be scanned with respect to the sample. Thus, in some embodiments, the probe is a surface scanning probe. Consequently, the electron spin resonance spectrometer can produce spatially-dependent spectra of the sample. It should be appreciated that the electron spin resonance spectrometer can acquire electron spin resonance spectra, for different types of samples, including a fluid sample (e.g., a gas or a liquid) or a solid sample. For a fluid sample, the fluid sample can be stationary or flowing with respect to the probe tip. Moreover, time-resolved electron spin resonance spectra can be acquired either by monitoring absorption at a fixed excitation frequency and fixed magnetic field strength or by monitoring absorption while scanning either the excitation frequency or magnetic field strength applied to the sample.

According to an embodiment, the electron spin resonance spectrometer has an acquisition time of less than or equal 10 s for a magnetic field strength scan width of 6 mT at an excitation frequency from 8 GHz to 9.5 GHz, e.g., at 8.845 GHz. In some embodiments, the acquisition time is less than or equal 1 s when the excitation frequency is scanned from 8 GHz to 8.5 GHz.

The electron spin resonance spectrometer is highly sensitive and has a high resolution. As indicated previously, the sample is subjected to the excitation frequency for the portion of the sample that is within the excitation volume of the probe tip. The excitation volume is determined, e.g., by the geometry or size of the probe tip. Therefore, it is contemplated that the sensitivity or resolution of the electron spin resonance spectrometer is dependent upon the excitation volume of the probe. The excitation volume of the probe is less than or equal to 100 mm$^3$, specifically less than or equal to 500 μm$^3$, more specifically less than or equal to 100 μm$^3$, more specifically less than or equal to 10 μm$^3$. In some embodiments, the excitation volume is from 1 μm$^3$ to 500 μm$^3$, more specifically less than or equal to 100 μm$^3$, more specifically less than or equal to 10 μm$^3$. Although the probe can be placed in a cavity, the electron spin resonance spectrometer herein does not include a cavity. As a result, no energy is stored from the excitation frequency in a region proximate to the probe tip. As such, the excitation frequency is reflected efficiently to the bridge from the probe in an absence of resonant absorption by the sample such that the excitation volume does not extend substantially beyond a near-field region of the probe tip. As used herein, the term "near-field" refers to a length of the wavelength of the excitation frequency. That is, the excitation volume extends from the probe tip to a distance of within one wavelength of the excitation frequency from the probe tip. Consequently, the probe is a near-field probe, wherein a distance from the sample to the probe tip is within one wavelength of the excitation frequency. Moreover, it is contemplated that a ratio of a volume of the sample to the excitation volume is greater than or equal to 1, specifically greater than or equal to 10, more specifically greater than or equal to 100, and further specifically greater than or equal to 1000. Since a cavity is not part of the electron spin resonance spectrometer, there is no limitation on a size of the sample, and a size of the probe or the probe tip can be tailored to be various sizes or shapes.

In terms of electron spins, the electron spin resonance spectrometer has a sensitivity greater than or equal to $5 \times 10^7$ spins, and can acquire spectra for less than $5 \times 10^7$ electron spins. In an embodiment, the electron spin resonance spectrometer has a sensitivity of a single electron spin. In terms of electron spin density of the sample, the electron spin resonance spectrometer can detect absorption of the excitation frequency for a sample with an electron spin density that is less than or equal to $5 \times 10^{13}$ spins, specifically less than or equal to $5 \times 10^{10}$ spins and more specifically less than or equal to $5 \times 10^7$ spins.

As used herein, the term "spatial resolution" (or simply "resolution") refers to a lateral distance of the probe with respect to how close adjacent unpaired electrons (e.g., defect sites in an electrical device such as a microprocessor chip) can be in the sample such that electron spin resonance absorption independently can be detected by the electron spin resonance spectrometer for each of the adjacent unpaired electrons. An electron spin resonance spectrometer has a high spatial resolution when a greater number of unpaired electrons per unit area independently can be detected via resonant absorption of the excitation frequency as compared with an electron spin resonance spectrometer that has a low spatial resolution where fewer unpaired electrons per unit area can be detected by resonant absorption. In certain embodiments, the electron spin resonance spectrometer is configured to obtain a spatial resolution less than or equal to 100 micrometers (μm), more specifically less than or equal to 1 μm, and more specifically less than or equal to 10 nm, including 5 μm or less, 3 μm or less, 1.5 μm or less, 1 μm or less, 800 nanometers (nm) or less, 500 nm or less, 100 nm or less, 50 nm or less, or 10 nm or less. In an embodiment, the electron spin resonance spectrometer has a spatial resolution from 10 nm to 10 μm.

The apparatus and processes herein are further illustrated by the following examples, which are non-limiting.

EXAMPLES

Example 1

Solid State Electron Spin Resonance Spectrum

Figure 19:
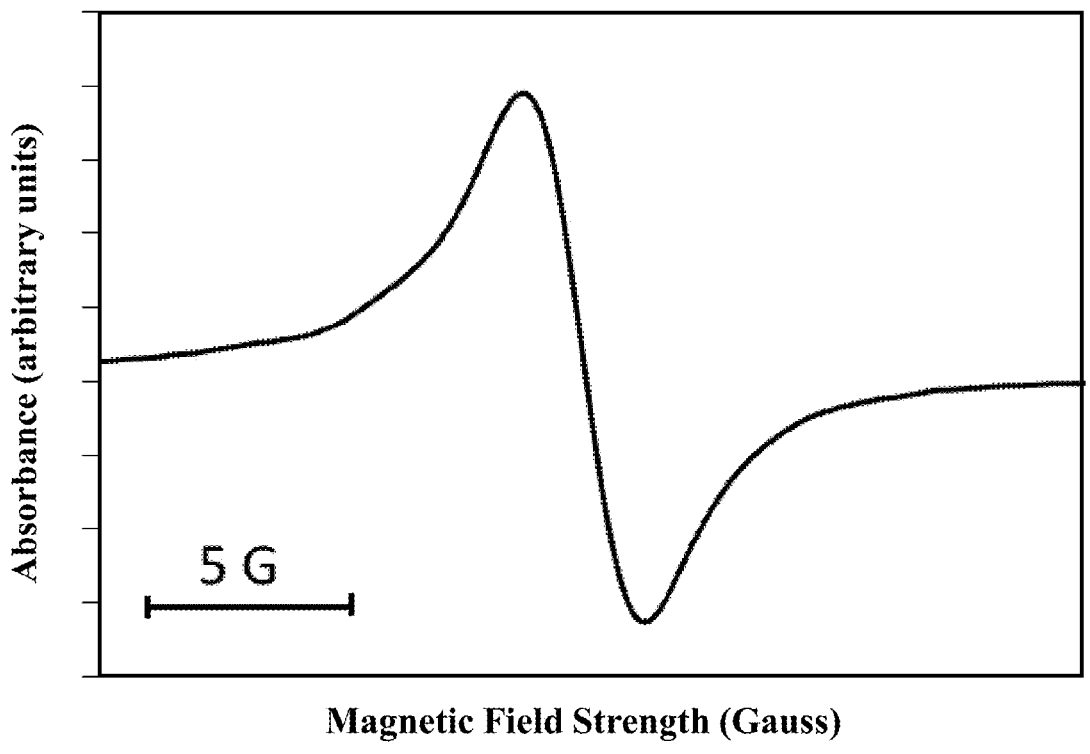
FIG. 19 shows a graph of absorption versus magnetic field strength for a solid sample of methyltriphenyl-arsonium tetracyanoquinodimethane according to Example 1.

A 7 microgram (μg) solid sample of methyltriphenylarsonium tetracyanoquinodimethane (methyltriphenyl-arsonium TCNQ) in crystalline form was disposed 1 nm from a probe tip of an electron spin resonance spectrometer. The sample was held at room temperature and ambient pressure and subjected to an excitation frequency of 8.845 GHz at a power of 2.5 mW at the tip of the probe. The excitation frequency had a full width at half-maximum (FWHM) bandwidth of 150 Hz centered about 8.845 GHz. The magnetic field strength was scanned 35 mT while being modulated at a reference frequency of 100 kHz at a modulation amplitude of approximately 3 G. A lock-in amplifier referenced to the reference frequency detected absorption by the sample. A resulting electron spin resonance (ESR) spectrum of the sample is shown in FIG. 19. The signal-to-noise ratio is extremely high, and no broadening is noticeable in the spectrum.

Example 2

ESR Spectra as a Function of Excitation Frequency

Figure 20:
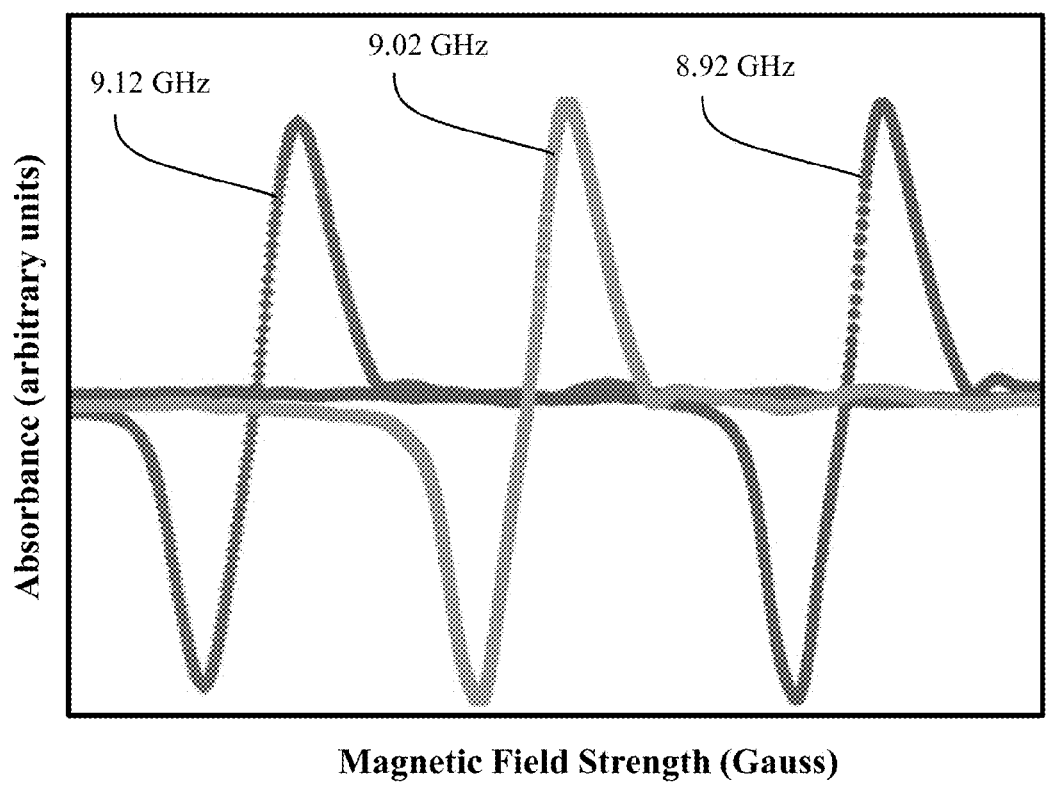
FIG. 20 shows a graph of absorption versus magnetic field strength for a solid sample of 2,2-diphenyl-1-picrylhydrazyl acquired for three different excitation frequencies according to Example 2.

A sample of 2,2-diphenyl-1-picrylhydrazyl (DPPH) was prepared in the same manner as the methyltriphenyl-arsonium TCNQ in Example 1. ESR spectra of the DPPH sample were acquired under substantially similar conditions as in Example 1, but the excitation frequency was set to 9.12 GHz, 9.02 GHz, or 8.92 GHz. The ESR spectrum at each excitation frequency is shown in FIG. 20. The zero-crossing point for each spectrum shifts to a different magnetic field strength as predicted by the Zeeman effect.

Example 3

Scanning Probe ESR Spectra

Figure 21:
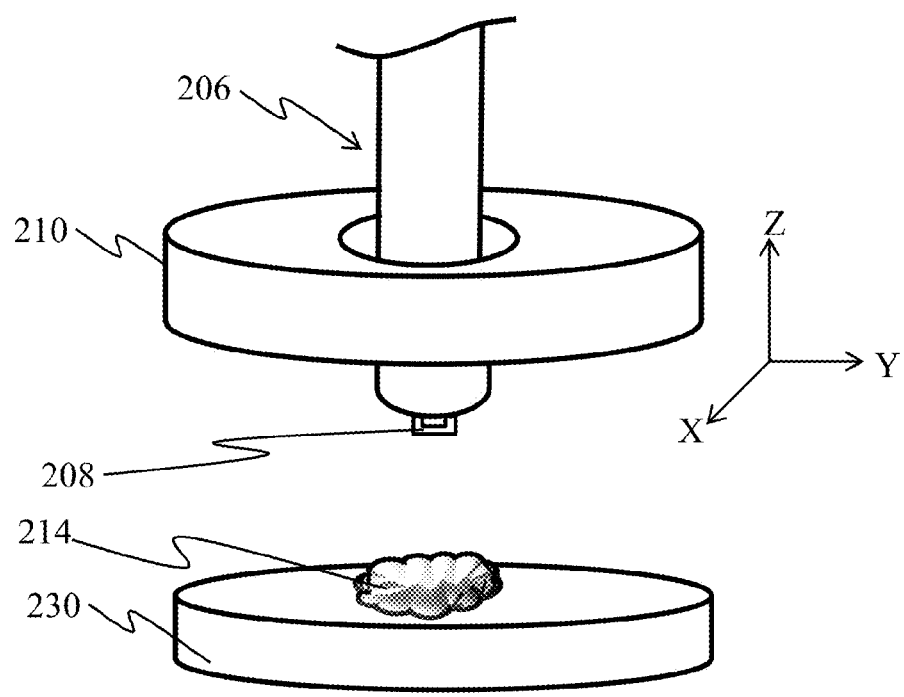
FIG. 21 shows an arrangement of an electron spin resonance spectrometer and a sample disposed on a stage according to Example 3.
Figure 22:
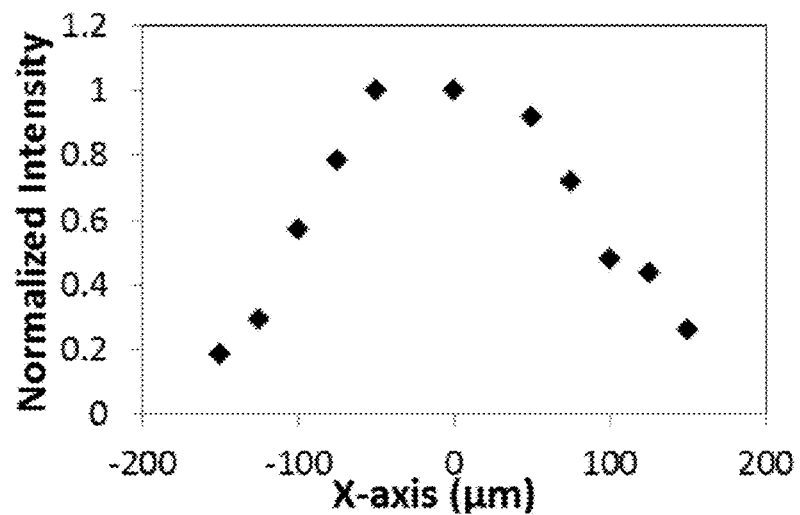
FIG. 22 shows a graph of normalized intensity versus x-axis position for a sample of methyltriphenyl-arsonium tetracyanoquinodimethane according to Example 3.
Figure 23:
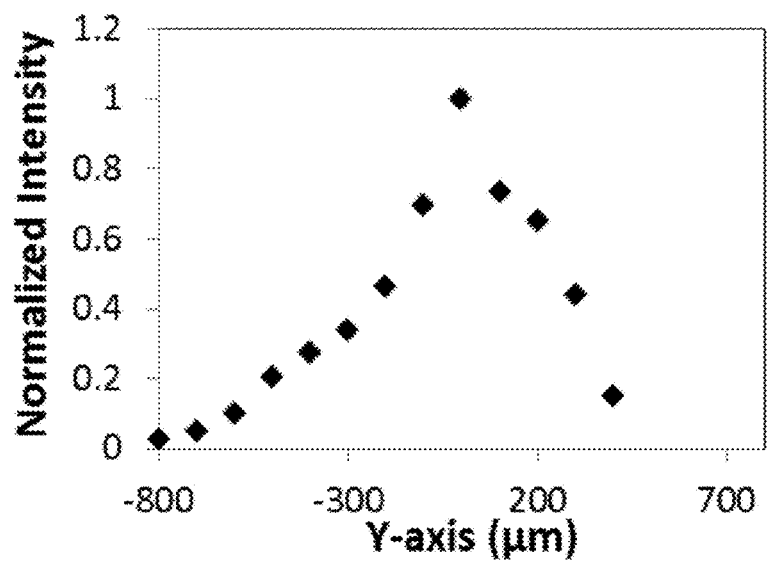
FIG. 23 shows a graph of normalized intensity versus y-axis position for a sample of methyltriphenyl-arsonium tetracyanoquinodimethane according to Example 3.
Figure 24:
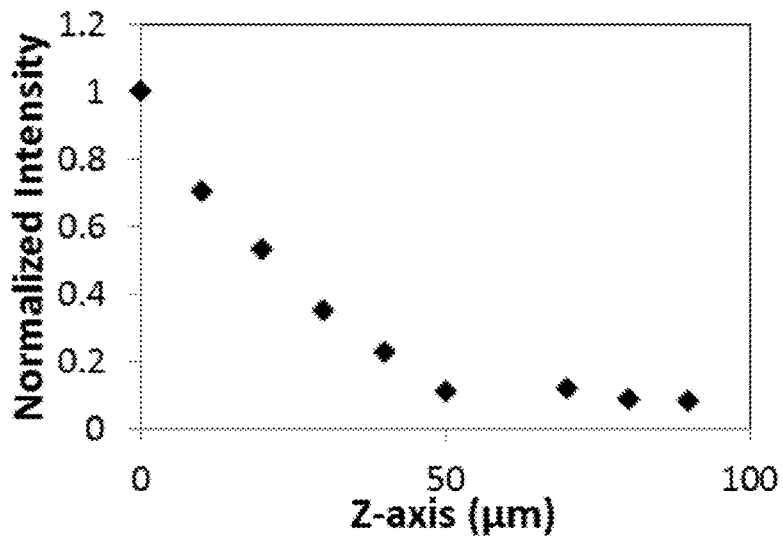
FIG. 24 shows a graph of normalized intensity versus z-axis position for a sample of methyltriphenyl-arsonium tetracyanoquinodimethane according to Example 3.

ESR spectra for the sample of Example 1 were acquired under identical conditions as in Example 1 except the sample was positioned with respect to the probe tip using a sample stage 230 (see FIG. 21) that had independent x-, y-, and z-positioning selectivity. The center of the sample was defined as the origin, i.e., (x, y, z)=(0, 0, 0). The sample 214 was moved with respect to the probe tip 208 by adjusting the sample stage 230. At each new position of the sample 214, an ESR spectrum was acquired, and the peak absorption was monitored as a function of position of the sample 214. For movement of the sample along the x-, y-, and z-coordinates (see inset of FIG. 21 for Cartesian coordinate system), normalized absorption versus position respectively is shown in FIGS. 22, 23, and 24. As expected, the normalized intensity decreases from the center of the sample (coordinate of about (0, 0, 0)).

Example 4

ESR Spectrum of a Liquid Sample

Figure 25:
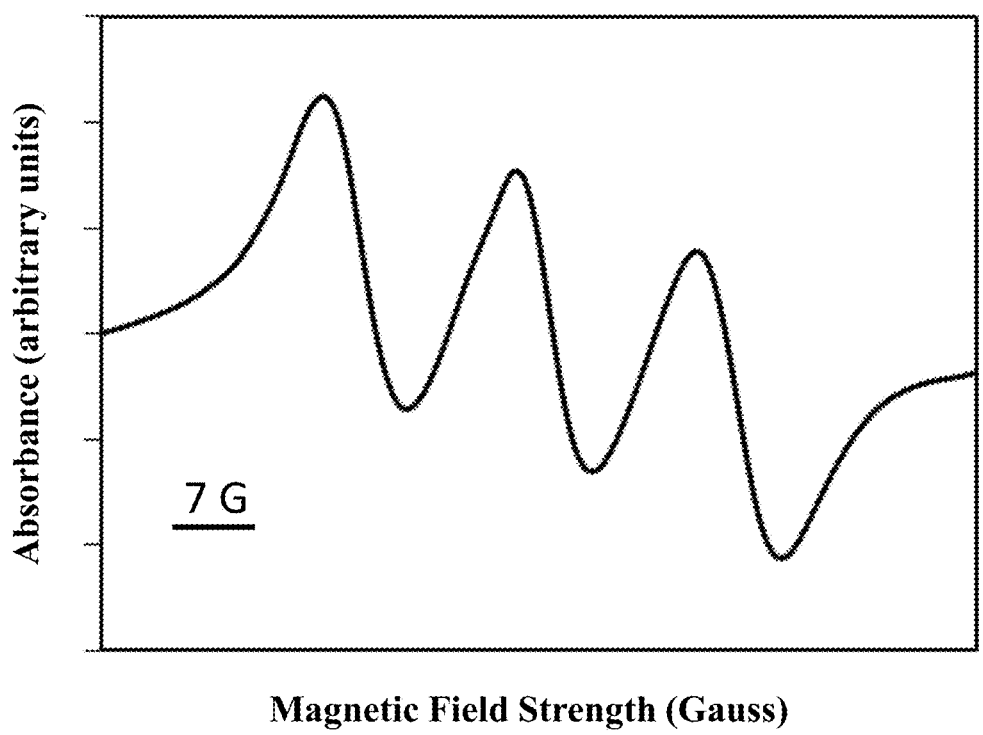
FIG. 25 shows a graph of absorption versus magnetic field strength for a liquid sample of 2,2,6,6-tetramethyl-1-piperidinyloxy according to Example 4.

A 300 nanoliter (nL), 0.25 molar (M) sample of 2,2,6,6-tetramethyl-1-piperidinyloxy (TEMPO) was prepared by dissolving TEMPO in ethylene glycol. The probe tip of the electron spin resonance spectrometer was immersed in the sample. The sample was held at room temperature and ambient pressure and subjected to an excitation frequency of 8.845 GHz at a power of 1 mW at the tip of the probe. The excitation frequency had a full width at half-maximum (FWHM) bandwidth of 150 Hz centered about 8.845 GHz. The magnetic field strength was scanned while being modulated at a reference frequency of 100 kHz at a modulation amplitude of approximately 3 G. A lock-in amplifier referenced to the reference frequency detected absorption by the TEMPO sample. The resulting electron spin resonance (ESR) spectrum of the TEMPO sample is shown in FIG. 25. The signal-to-noise ratio is extremely high, and no broadening is noticeable in the spectrum.

While one or more embodiments have been shown and described, modifications and substitutions may be made thereto without departing from the spirit and scope of the invention. Accordingly, it is to be understood that the present invention has been described by way of illustrations and not limitation. Embodiments herein can be used independently or can be combined.

All ranges disclosed herein are inclusive of the endpoints, and the endpoints are independently combinable with each other. The ranges are continuous and thus contain every value and subset thereof in the range. Unless otherwise stated or contextually inapplicable, all percentages, when expressing a quantity, are weight percentages. The suffix "(s)" as used herein is intended to include both the singular and the plural of the term that it modifies, thereby including at least one of that term (e.g., the colorant(s) includes at least one colorants). "Optional" or "optionally" means that the subsequently described event or circumstance can or cannot occur, and that the description includes instances where the event occurs and instances where it does not. As used herein, "combination" is inclusive of blends, mixtures, alloys, reaction products, and the like.

As used herein, "a combination thereof" refers to a combination comprising at least one of the named constituents, components, compounds, or elements, optionally together with one or more of the same class of constituents, components, compounds, or elements.

All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." It should further be noted that the terms "first," "second," "primary," "secondary," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity). The conjunction "or" is used to link objects of a list or alternatives and is not disjunctive; rather the elements can be used separately or can be combined together under appropriate circumstances.

What is claimed is:

1. An electron spin resonance spectrometer comprising:
   a bridge to transmit an excitation frequency and to receive a signal frequency;
   a probe electrically connected to the bridge and comprising:
      a first conductor in electrical communication with the bridge to transmit the signal frequency to the bridge;
      a shorting member electrically connected to the first conductor to transmit the excitation frequency to a sample, to produce the signal frequency, and to transmit the signal frequency to the first conductor; and
      a second conductor electrically connected to the shorting member; and
   a magnet disposed proximate to the probe.

2. The electron spin resonance spectrometer of claim 1, further comprising a modulation coil disposed on a surface of the magnet such that the modulation coil is interposed between the magnet and the sample,
   wherein the modulation coil is configured to receive a bias voltage, a reference frequency, or a combination comprising at least one of foregoing.

3. The electron spin resonance spectrometer of claim 2, further comprising a detector connected to the bridge to detect a detection frequency.

4. The electron spin resonance spectrometer of claim 3, wherein the bridge comprises:
   a reference arm to transmit the excitation frequency to a combiner;
   a sample arm comprising a circulator and configured to transmit the signal frequency and the excitation frequency reflected by the shorting member to the combiner; and
   the combiner to balance the bridge and to transmit a combined frequency toward the detector,
   wherein the bridge is configured to be balanced in the absence of the signal frequency at the combiner, and the bridge is configured to be unbalanced in the presence of the signal frequency at the combiner.

5. The electron spin resonance spectrometer of claim 4, wherein the bridge further comprises a local oscillator arm comprising a mixer, the bridge being configured to produce the detection frequency and to transmit the detection frequency to the detector.

6. The electron spin resonance spectrometer of claim 3, wherein the detector is a phase sensitive detector.

7. The electron spin resonance spectrometer of claim 6, further comprising a reference oscillator configured to transmit the reference frequency to the modulation coil and to the detector.

8. The electron spin resonance spectrometer of claim 1, further comprising an excitation source to produce the excitation frequency and to transmit the excitation frequency to the bridge.

9. The electron spin resonance spectrometer of claim 1, wherein the electron spin resonance spectrometer is configured to acquire an electron spin resonance spectrum in response to varying the excitation frequency present at the shorting member, a magnetic field strength applied to the sample from the magnet, or a combination comprising at least one of the foregoing.

10. The electron spin resonance spectrometer of claim 1, wherein the shorting member is a lumped circuit comprising:
   a first conductor extension electrically connected to the first conductor;
   a second conductor extension electrically connected to the second conductor; and
   a probe tip electrically shorting the first conductor to the second conductor, the probe tip configured to transmit the excitation frequency to the sample.

11. The electron spin resonance spectrometer of claim 10, wherein the shorting member further comprises a basal member such that the first conductor extension and the second conductor extension are disposed on the basal member, and
   the probe tip extends from the first conductor extension and the second conductor extension such that a portion of the probe tip is not disposed on the basal member.

12. The electron spin resonance spectrometer of claim 10, wherein a length of the probe tip that is configured to transmit the excitation frequency to the sample has a length from 500 nm to 500 μm.

13. The electron spin resonance spectrometer of claim 1, wherein the magnet is surroundingly disposed around the probe.

14. The electron spin resonance spectrometer of claim 13, wherein the electron spin resonance spectrometer is configured to acquire an electron spin resonance spectrum with the excitation frequency from 1 MHz to 100 GHz, inclusive of each excitation frequency.

15. The electron spin resonance spectrometer of claim 1, wherein the electron spin resonance spectrometer has an excitation volume of less than 100 μm$^3$.

16. The electron spin resonance spectrometer of claim 1, wherein the electron spin resonance spectrometer is configured to receive the sample being disposed proximate to the shorting member and external to the magnet.

17. The electron spin resonance spectrometer of claim 1, wherein the electron spin resonance spectrometer is configured to acquire an electron spin resonance spectrum in the absence of a cavity.

18. The electron spin resonance spectrometer of claim 1, wherein the probe is a surface scanning probe.

19. The electron spin resonance spectrometer of claim 1, wherein the probe is a non-resonant, near-field probe.

20. A method for acquiring an electron spin resonance spectrum, the method comprising:
   disposing a sample in an electron spin resonance spectrometer comprising:
      a bridge comprising a sample arm and a reference arm;
      a probe electrically connected to the bridge and comprising:
         a first conductor electrically connected to the bridge;
         a shorting member electrically connected to the first conductor; and
         a second conductor electrically connected to the shorting member;
      a detector electrically connected to the bridge;
      a magnet disposed proximate to the probe and the sample; and
      a modulation coil interposed between the magnet and the sample;
   transmitting an excitation frequency from an excitation source to the sample through the sample arm and the shorting member;
   modulating a magnetic field present at the sample from the magnet at a reference frequency applied to the modulation coil;
   absorbing, by the sample, the excitation frequency;
   producing a signal frequency at the shorting member;
   transmitting the signal frequency from the shorting member toward the detector;
   combining the signal frequency from the sample arm and the excitation frequency from the reference arm to produce a detection frequency; and
   detecting, by the detector, the detection frequency as a function of changing the excitation frequency or a magnetic field strength present at the sample to acquire the electron spin resonance spectrum,
   wherein the sample is disposed external to the probe, the magnet, and the modulation coil.

* * * * *